United States Patent [19]

Rosebrough

[11] Patent Number: 5,326,778
[45] Date of Patent: Jul. 5, 1994

[54] CONJUGATES OF BIOTIN AND DEFEROXAMINE FOR RADIOIMMUNOIMAGING AND RADIOIMMUNOTHERAPY

[75] Inventor: Scott F. Rosebrough, Avon, N.Y.

[73] Assignee: Research Corporation Technologies, Inc., Tucson, Ariz.

[21] Appl. No.: 845,416

[22] Filed: Mar. 3, 1992

[51] Int. Cl.$^5$ .................. C07D 495/04; A61K 31/415
[52] U.S. Cl. ................................. 514/387; 548/304.1; 424/2; 424/9
[58] Field of Search ...................... 548/304.1; 424/1.1, 424/2, 9; 514/387

[56] References Cited

U.S. PATENT DOCUMENTS

| | | | |
|---|---|---|---|
| 4,454,106 | 6/1984 | Gansow et al. | 424/1.1 |
| 4,680,338 | 7/1987 | Sundoro et al. | 525/54.1 |
| 4,863,713 | 9/1989 | Goodwin et al. | 424/1.1 |
| 4,888,163 | 12/1989 | Kubodera et al. | 424/1.1 |
| 4,943,427 | 7/1990 | Yazaki et al. | 424/1.1 |

FOREIGN PATENT DOCUMENTS 8907097 8/1989 PCT Int'l Appl. .

OTHER PUBLICATIONS

Hnatowich et al. (1987) "Investigations of Avidin and Biotin for Imaging Applications" *J. Nucl. Med.* 28, 1294–1302.

Kalofonos, et al. (1990) "Imaging of Tumor in Patients with Indium-111-Labeled Biotin and Streptavidin-Conjugated Antibodies: Preliminary Communication" *J. Nucl. Med.* 31, 1791–1796.

Ohmomo, et al. (1982) "$^{67}$Ga–Labeled Human Fibrinogen: A New Promising Thrombus Imaging Agent" *Eur. J. Nucl. Med.* 7, 458–461.

Paganelli, et al. (1988) "In vivo Labelling of Biotinylated Monoclonal Antibodies by Radioactive Avidin: A Strategy to Increase Tumor Radiolocalization" *Int. J. Cancer* 2, 121–125.

Parker (1990) "Tumour Targeting" *Chemistry in Britain*, 942–945.

Takahashi, et al. (1985) "Preparation and Biodistribution of $^{67}$Ga-Labelled Fibrinogen Conjugated with a Water–Soluble Polymer Containing Deferoxamine" *Vienna IAEA*, 471–482.

Weiner, et al. (1979) "Relative Stability of In-111 and Ga-67 Desferrioxamine and Human Transferrin Complexes" *Proceedings of the Second International Symposium on Radiopharmaceuticals*, 331–340.

Yamamoto, et al. (1988) "Positive Imaging of Venous Thrombi and Thromboemboli with Ga-67 DFO-DAS-Fibrinogen" *Eur. J. Nucl. Med.* 14, 60–64.

Yokoyama, et al. (1981) "Deferoxamine, A Promising Bifunctional Chelating Agent for Labeling Proteins with Gallium: Ga-67 DF-HSA: Concise Communication" *J. Nucl. Med.* 23, 909–914.

*Primary Examiner*—Joseph Paul Brust
*Assistant Examiner*—Mary Susan H. Gabilan
*Attorney, Agent, or Firm*—Scully, Scott, Murphy & Presser

[57] ABSTRACT

The present invention provides compounds which are covalent conjugates of deferoxamine and biotin or derivatives thereof. The subject compounds are capable of binding metal ions and avidin or streptavidin, and accordingly are useful in two-step radioimmunoimaging and radioimmunotherapy. Methods for the synthesis of the deferoxamine-biotin conjugates are also provided by the present invention.

12 Claims, 7 Drawing Sheets

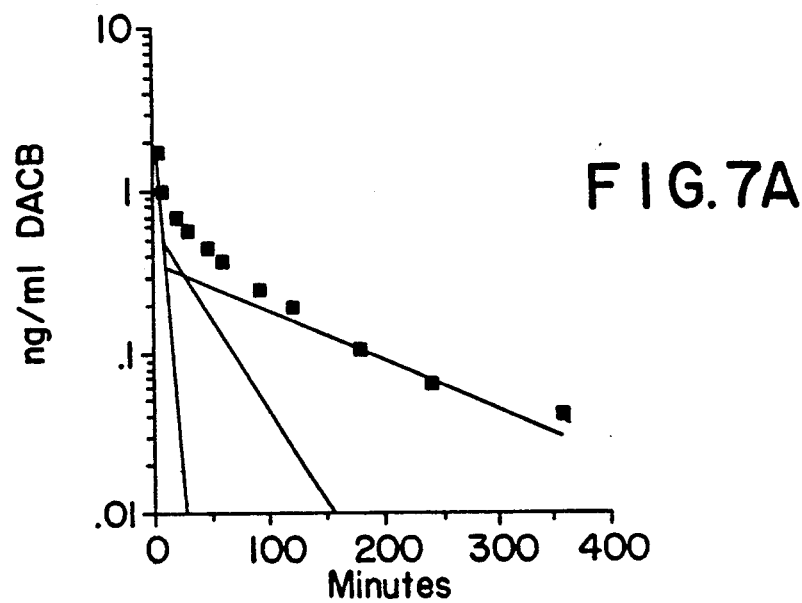
FIG. 7A Plasma Pharmacokinetics of Ga-67 DACB
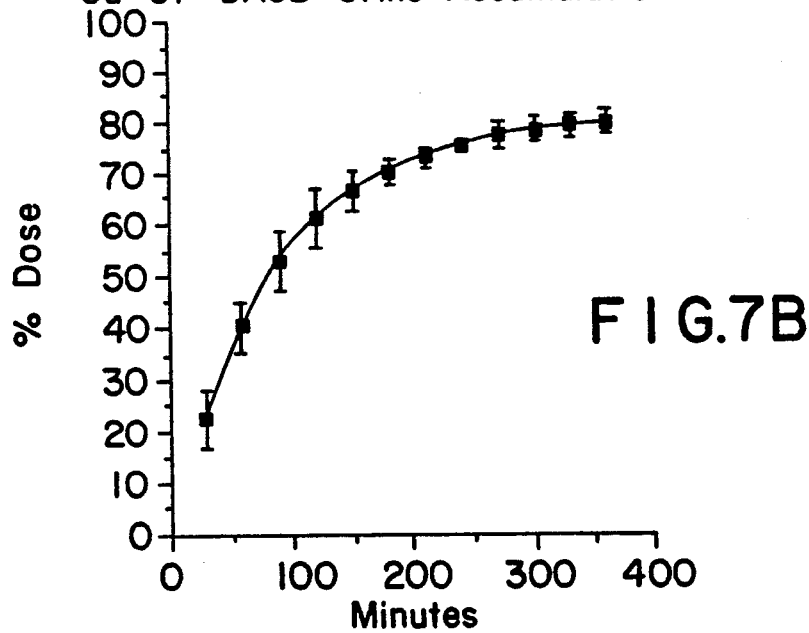
FIG. 7B Ga-67 DACB Urine Accumulation

CONJUGATES OF BIOTIN AND DEFEROXAMINE FOR RADIOIMMUNOIMAGING AND RADIOIMMUNOTHERAPY

This invention was made with government support under Contract No. HL-24230-11 awarded by the National Institutes of Health. The government has certain rights in the invention.

FIELD OF THE INVENTION

The present invention provides biotin derivatives suitable for radiolabeling and useful in two-step radioimmunoimaging and radioimmunotherapy. In particular, the present invention is directed to covalent conjugates of biotin and deferoxamine which are stable in vivo and suitable for radiolabeling. In the two-step approach, radiolabeled biotin derivatives are used to deliver radionuclides suitable for imaging and therapy to target-bound streptavidin or avidin conjugated antibodies or other cell-targeting agents.

BACKGROUND OF THE INVENTION

Radioimaging and radiotherapy utilize cell or tissue specific targeting agents as delivery systems for radioactive, paramagnetic or cytotoxic agents. Any agent which is specific for a lesion or site of interest can potentially act as a targeting agent. For example, polyclonal and monoclonal antibodies can be produced which exhibit considerable specificity for certain cell or tissue types. Many other agents, including toxins such as diphtheria toxin, exhibit cell specificity and can be used to deliver diagnostic or therapeutic agents. The technique of delivery of monoclonal antibodies (MAbs) has been investigated for cancer therapy as well as for diagnosis of cancer, thromboembolism and cardiac myopathy. For successful radioimmunoimaging, sufficient labeled MAb must localize at the target site to provide enough signal for detection. Target-to-background ratios must be high in order to achieve adequate contrast between target-bound radioactivity and background levels in other organs, tissues and blood. A major obstacle to successful radioimmunoimaging is the high background activity of free circulating radiolabeled MAbs due to prolonged circulation and accumulation in liver and spleen, the normal metabolic sites for Abs. Furthermore, the toxic effects of high radiation doses must be considered in both radioimmunotherapy and radioimmunoimaging. Such obstacles are also a consideration for methods utilizing targeting agents other than monoclonal antibodies.

To overcome such obstacles, "pre-targeting" or "two-step" approaches have been investigated. In the conventional one-step method the radionuclide is linked to the MAb either directly or via a bifunctional chelating agent. In the two-step approach the antibody is unlabeled. Unlabeled antibody is administered, and antibody which does not localize to the target site is allowed to clear from circulation before the administration of radioactivity. The radioactivity is then administered in a chemical form which has high affinity for the antibody.

To provide the diagnostic or imaging agent in a form with high affinity for the antibody, two-step methods have been designed to exploit the high affinity of avidin and streptavidin for biotin. Avidin, a 67 kilodalton (kD) glycoprotein found in egg whites, has an exceptionally high binding affinity ($K_a = 10^{-15}$) for biotin. Avidin consists of four subunits, each capable of binding one biotin molecule. Streptavidin, a similar protein produced in *Streptomyces avidinii*, shares significant conformation and amino acid composition with avidin, as well as high affinity and stability for biotin. However, streptavidin is not glycosylated and reportedly exhibits less non-specific binding to tissues. Streptavidin is widely used in place of avidin because of its lower non-specific binding. Biotin, a member of the B-complex vitamins, is essential for amino acid and odd-chain fatty acid degradation, gluconeogenesis and fatty acid synthesis and is normally found in the enzyme bound form as biocytin.

The use of the two-step avidin-biotin or streptavidin-biotin approach for radioimmunoimaging and radioimmunotherapy is theoretically attractive since: 1) biotin and avidin are likely to be nontoxic at the levels required for these applications; 2) the high affinity of avidin and biotin results in the in vivo stability of the avidin-biotin bond; 3) the rapid clearance of biotin through the kidney avoids problems associated with use of radiolabeled MAbs; and 4) the tetravalency of avidin and streptavidin for biotin allows for amplification of the signal at the target site.

In the two-step avidin-biotin or streptavidinbiotin approach, antibodies are coupled with either biotin or avidin and administered to the subject, followed by administration of radiolabeled avidin or biotin, respectively. Using an animal non-tumor model, Hnatowich et al. [(1987) *J. Nucl. Med.* 28, 1294] have demonstrated the administration of avidin-conjugated antibody to mice, followed by administration of $^{111}$In-labeled biotin. Imaging was performed to determine the ratio of radioactivity in the target organ relative to other organs. Using Protein A-conjugated beads to simulate tumor, Hnatowich et al. thus demonstrated localization of the label to the target, with improved target-to-nontarget ratios relative to the conventional one-step approach. In a similar study, Paganelli et al. [(1988) *Int. J. Cancer* 2, 121] demonstrated the in vivo labeling of biotinylated antibody with $^{131}$I-and $^{111}$In-labeled avidin.

Kalofonos et al. [(1990) *J. Nucl. Med.* 31, 1791] have reported preliminary results of a limited clinical trial in which patients with squamous cell carcinoma of the lungs received streptavidin-conjugated monoclonal antibody followed by $^{111}$In-labeled biotin. In eight out of ten patients, tumor was detected with labeled biotin alone without the previous administration of streptavidin-conjugated antibody, perhaps due to localization of labeled biotin in tumor. In three of these patients, images were improved with the prior administration of antibody. The fact that targeting was not improved in all patients was speculated to be due to rapid internalization of antibody but may be the result of uptake of biotin by tumor cells.

Clinical studies demonstrating a two-step approach (biotinylated MAb followed by $^{111}$In-labeled streptavidin) and a three-step approach (biotinylated MAb followed by cold avidin followed by $^{111}$In-labeled biotin) have also been reported by Paganelli et al. [(1990) *J. Nucl. Med.* 31, 735].

In the above studies, biotin, avidin and streptavidin were each labeled with $^{111}$In via the bifunctional chelating agent diethylentriaminepentaacetic acid (DTPA) by the bicyclic anhydride method of Hnatovich et al. [(1982) *Int. J. Appl. Radiat. Isotop.* 33, 327].

A bifunctional chelating agent is a reagent which has the ability to bind to a metal ion as well as to bind to a protein or antibody. The use of chelating agents to radiolabel biotin has advantages over direct labeling since the resulting complexes are more likely to be stable and to retain biological activity. However, the use of DTPA as a chelating agent to label biotin presents significant limitations to the development of two-step radioimmunoimaging and radioimmunotherapy. DTPA-biotin is a dimer containing two biotin molecules (biotin-DTPA-biotin). Since each molecule of avidin binds four biotin molecules, a maximum of two molecules of DTPA-biotin can bind per mole of avidin or avidin-conjugated antibody, thus limiting the amount of radioactivity that can be delivered to the target site.

Another disadvantage of DTPA-biotin as a labeling reagent is a consequence of the conjugation of DTPA and biotin. DTPA-biotin is prepared by covalently linking DTPA to biotin through the use of the cyclic anhydride of DTPA and biocytin, a lysine conjugate of biotin with an available primary amine for conjugation (Hnatowich, 1987). DTPA is a member of the aminocarboxylic acid class of chelating agents, having five deprotonated carboxylate groups and three tertiary amino groups for binding to the metal ion. Since two of the five COO$^-$ groups are used for conjugation to biocytin, DTPA is rendered hexadentate rather than octadentate, leading to decreased thermodynamic stability and consequent label instability. Maecke et al. [(1989) *J. Nucl. Med.* 30, 1235] have demonstrated that the octadentate ligand of $^{111}$In-DTPA is superior to ligands with smaller denticity for in vivo applications.

A further disadvantage of DTPA as a chelating agent is its affinity for divalent cations found in vivo, especially $Mg^{2+}$ and $Ca^{2+}$ (stability constants of 9 and 11, respectively). The affinity of DTPA for divalent cations allows for the exchange of the radiometal with divalent metal in in vivo applications. For example, In and Y are released from DTPA-MAbs at a rate of about 10 percent per day in vivo [Hnatowich et al., (1985) *J. Nucl. Med.* 26, 503], and would be replaced by $Ca^{2+}$ and $Mg^{2+}$, which are present in much higher concentrations. In addition to reducing the amount of radiometal delivered to the target site, a further problem is created by the exchange of radiometal for divalent cation. Certain released radiometals will become bound by transferrin, a human plasma metal binding protein. For example, the affinity of transferrin for Fe and Ga is higher than the affinity of DTPA for these metals, thus promoting the leaching of Fe and Ga off of DTPA and onto transferrin. The consequence of this leaching is the eventual sequestration of the radiometal-transferrin complex to the liver and bone marrow, a tissue which is particularly susceptible to radiation damage.

Another consequence of the affinity of DTPA for divalent cations is a reduction in labeling efficiency due to the presence of these competing impurities in radionuclide solutions.

A still further disadvantage of DTPA occurs because the affinity of DTPA for metal ions is pH sensitive. Since the deprotonated form is the chelating moiety, metal binding affinity is decreased at low pH, a condition which may be present in tumors and abscesses. Brechbiel et al. [(1986) *Inorgan. Chem.* 25, 2772] and Meares [(1986) *Nucl. Med. Biol.* 13, 311], have reported that anionic complexes of DTPA with Cu, In or Y are susceptible to acid- or cation-catalyzed dissociation, and that free metal ions are prematurely released in vivo with a propensity to accumulate in liver, bone and bone marrow.

Accordingly, a need exists for better biotin conjugates which can be labeled with radionuclides suitable for diagnosis and therapy. The present invention provides conjugates of deferoxamine and biotin which overcome the deficiencies of the compounds of the prior art.

Deferoxamine (DFO) is a trivalent metal chelating agent with extremely high affinity for transition metals [e.g. $K_d = 10^{-30}M^{-1}$ for iron(III)]. It contains three hydroxamic groups and reacts stoichiometrically with tripositive metal ions to form octahedral complexes. Deferoxamine mesylate is commercially available and has been established as a safe drug for the short-term treatment of iron toxicity, iron storage disease and iron and aluminum overload. Due to its high affinity for other metals, DFO is potentially useful in certain modalities of radiology, including nuclear medicine and magnetic resonance imaging, when bound to radioactive metals such as $^{99m}$Tc, $^{111}$In, $^{67}$Ga, $^{90}$Y, $^{186}$Re, $^{18}$Re, $^{212}$Bi, or paramagnetic ions such as Fe and Gd. DFO forms stable metal chelates, and has a reactive amino group available for coupling with proteins.

DFO forms an uncharged chelate of compact structure, thus minimizing its effect on the biological properties of the protein to which it is conjugated. DFO has been used to prepare $^{67}$Ga-labeled human serum albumin [Yokoyama et al. (1981) *J. Nucl. Med.* 23, 909] and $^{67}$Ga-labeled fibrinogen [Ohmomo et al. (1982) *Eur. J. Nucl. Med.* 7, 458]. Takahashi et al. [(1985) *Viena IAEA* 471], provide a method for increasing the specific activity of $^{67}$Ga-labeled fibrinogen by coupling DFO to fibrinogen through a functional polymer, dialdehyde starch (DAS), to provide a $^{67}$Ga-fibrinogen-(DAS-DFO) conjugate. Yamamoto et al. [(1988) *Eur.J. Nucl. Med.* 14, 60], have evaluated $^{67}$Ga-fibrinogen-(DAS-DFO) for imaging of venous thrombi. U.S. Pat. No. 4,680,338 to Sundoro discloses a bifunctional sequential linker and its use to minimize crosslinking of amine ligands, and contemplates its use in the preparation of a DFO-antibody conjugate. Kubodera et al. (U.S. Pat. No. 4,888,163) and Yazaki et al. (U.S. Pat. No. 4,943,427) also contemplate the preparation of a radiolabeled DFO-antibody conjugate.

DFO provides significant advantages over DTPA as a bifunctional chelating agent for two-step radioimmunoimaging and radioimmunotherapy. DFO has one primary amine available for coupling reactions with proteins, and thus a DFO-biotin conjugate would be expected to be a monomer, i.e. one molecule of DFO per molecule of biotin. Accordingly, a DFO-biotin conjugate has the potential to deliver twice the molar amount of metal per biotin molecule relative to a, dimer of DTPA-biotin. Furthermore, the amine group available for conjugation to biotin is spaced by five carbon atoms from the nearest hydroxamic group involved in chelation. Thus, in contrast to DTPA-biotin, conjugation of biotin to DFO should not appreciably affect the affinity of DFO for metal ions.

Another advantage of DFO as a bifunctional chelating agent is its low affinity for divalent metals. The stability constants of $Ca^{2+}$ and $Mg^{2+}$ with DFO are 3 and 4, respectively. Accordingly, exchange of radiometal with $Ca^{2+}$ and $Mg^{2+}$, which are present in high concentrations in body fluids and buffers, is minimal.

Weiner et al. [(1979) in *Proceedings of the Second International Symposium on Radiopharmaceuticals*, 331], have demonstrated that a $^{67}$Ga-DFO complex is much stronger than a $^{67}$Ga-transferrin complex. This provides another advantage of DFO, in that the leaching of certain metals to transferrin is eliminated.

Since DFO has no ionizable groups, its affinity for metals is not sensitive to low pH, which is yet another advantage over DTPA as a chelating agent.

Accordingly, the present invention provides stable conjugates of DFO and biotin for use in radioimmunoimaging and radioimmunotherapy. As discussed hereinabove, the compounds of the present invention have been developed to overcome the deficiencies of the commercially available biotin derivative, DTPA-biotin, which is a conjugate of DTPA and biocytin. Biocytin is a lysine conjugate of biotin which is the main form of biotin in foodstuffs, and is useful for synthesis of biotin derivatives since it is readily conjugated due to the availability of a primary amine. Biocytin is commercially available in its N-protected form as succinimidyl-6-(biotinamide)hexanoate (NHS-LC-biotin). However, it has been discovered in accordance with the present invention that a conjugate of biocytin covalently bonded to DFO (defero-desaminolysyl-biotin, DLB) is unstable, as demonstrated hereinbelow, and therefore unsuitable for use in two-step imaging and therapy. The DFO-biotin conjugate is rapidly degraded to biotin and desaminolysyldeferoxamine. The site of cleavage mimics the site in biocytin at which digestion by biotinidase occurs. Biotinidase is an enzyme found in high concentrations in plasma, gut, liver and other tissues which catalyzes the hydrolysis of biocytin to biotin and free lysine as follows provide DFO-biotin conjugates which are not subject to rapid degradation by biotinidase.

SUMMARY OF THE INVENTION

This invention relates to compounds which are conjugates of biotin and deferoxamine, and derivatives thereof, which are stable in vivo and capable of binding avidin and streptavidin. DFO-biotin conjugates, as defined o herein, refers to compounds which comprise DFO covalently linked to biotin, either directly or via a linking group. Derivatives of DFO-biotin conjugates, as defined herein, encompasses any covalent or non-covalent modification such that the conjugate retains metal-chelating and avidin-binding ability. In a preferred embodiment, the compound is deferobiotin (DB) and is represented by the formula

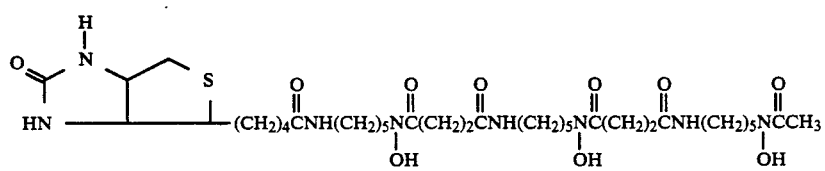

In another preferred embodiment, the compound is deferoacetyl-cysteinyl-biotin (DACB) and is represented by the formula

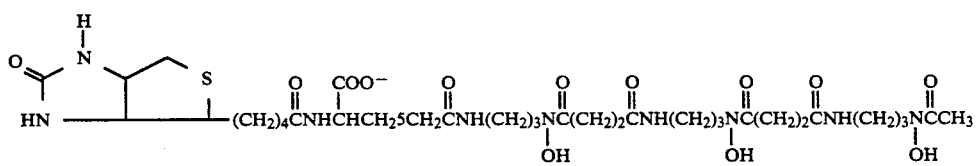

In another aspect of the present invention, the compounds are chelated with a metal ion or radioactive metal.

The present invention further provides a method for the synthesis of conjugates of biotin and deferoxamine, especially for the synthesis of deferobiotin and deferoacetyl-cysteinyl-biotin.

A further aspect of the present invention provides methods of radioimmunoimaging and radioimmunotherapy with the biotin-deferoxamine conjugates provided herein. The method of radioimmunoimaging

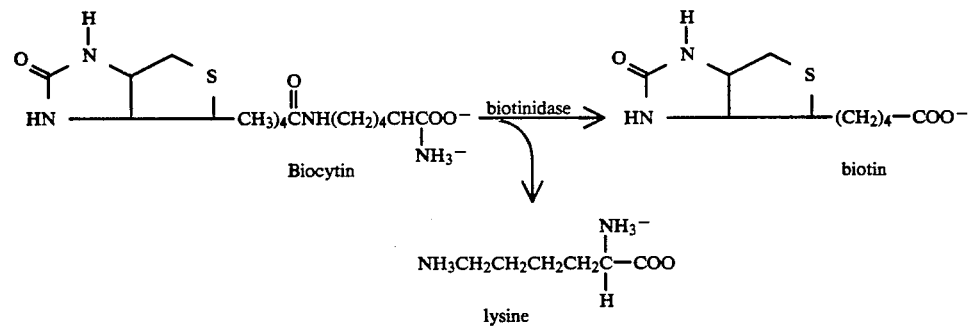

Biotinidase also digests short biotinyl peptides. It has been demonstrated that biotinidase is not a general proteolytic enzyme, but rather has .specific structural requirements in the substrate for hydrolysis [Chauhan et al. (1986) *J. Biol. Chem.* 261, 4268]. Therefore, it has become a further object of the present invention to comprises administering an avidin or streptavidin conjugated monoclonal antibody to a host in an amount sufficient to bind to the target site, followed by administering the deferoxamine-biotin compound of the present invention labeled with a paramagnetic or radioactive metal under conditions to form a complex with said monoclonal antibody and at a dose sufficient for detection. The resulting complex is then detected.

The method of radioimmunotherapy comprises administering an avidin or streptavidin conjugated monoclonal antibody to a host in an amount sufficient to bind to the target site, followed by administering the deferoxaminebiotin compound of the present invention labeled with a radioactive metal at a therapeutic dose and under conditions to form a complex with said monoclonal antibody.

plasma for six hours, relative to unincubated conjugates, as measured by the avidin binding assay as described hereinbelow.

A preferred compound of the invention is deferobiotin (DB), a covalent conjugate of deferoxamine and biotin represented by the formula

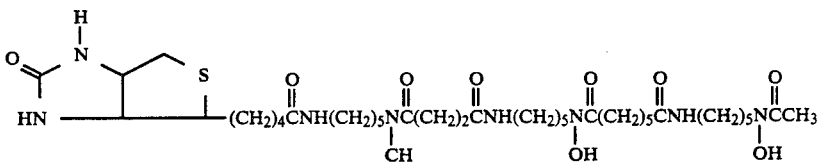

Another preferred compound of the invention is defero-acetyl-cysteinyl-biotin (DACB), a covalent conjugate of iodoacetyl-deferoxamine and cysteinyl-biotin represented by the formula

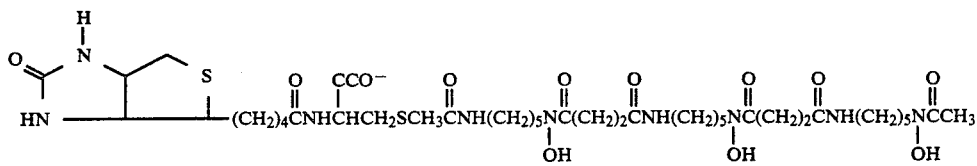

Yet another aspect of the present invention provides pharmaceutical compositions containing the subject biotin-deferoxamine conjugates and a pharmaceutically acceptable carrier.

A compartmentalized kit for radioimaging or radiotherapy is also provided by the present invention.

BRIEF DESCRIPTION OF THE DRAWINGS

FIG. 7A demonstrates the plasma pharmacokinetics of $^{67}$Ga-DACB. FIG. 7B depicts the urine accumulation of $^{67}$Ga-DACB.

DETAILED DESCRIPTION OF THE INVENTION

Figure 1:
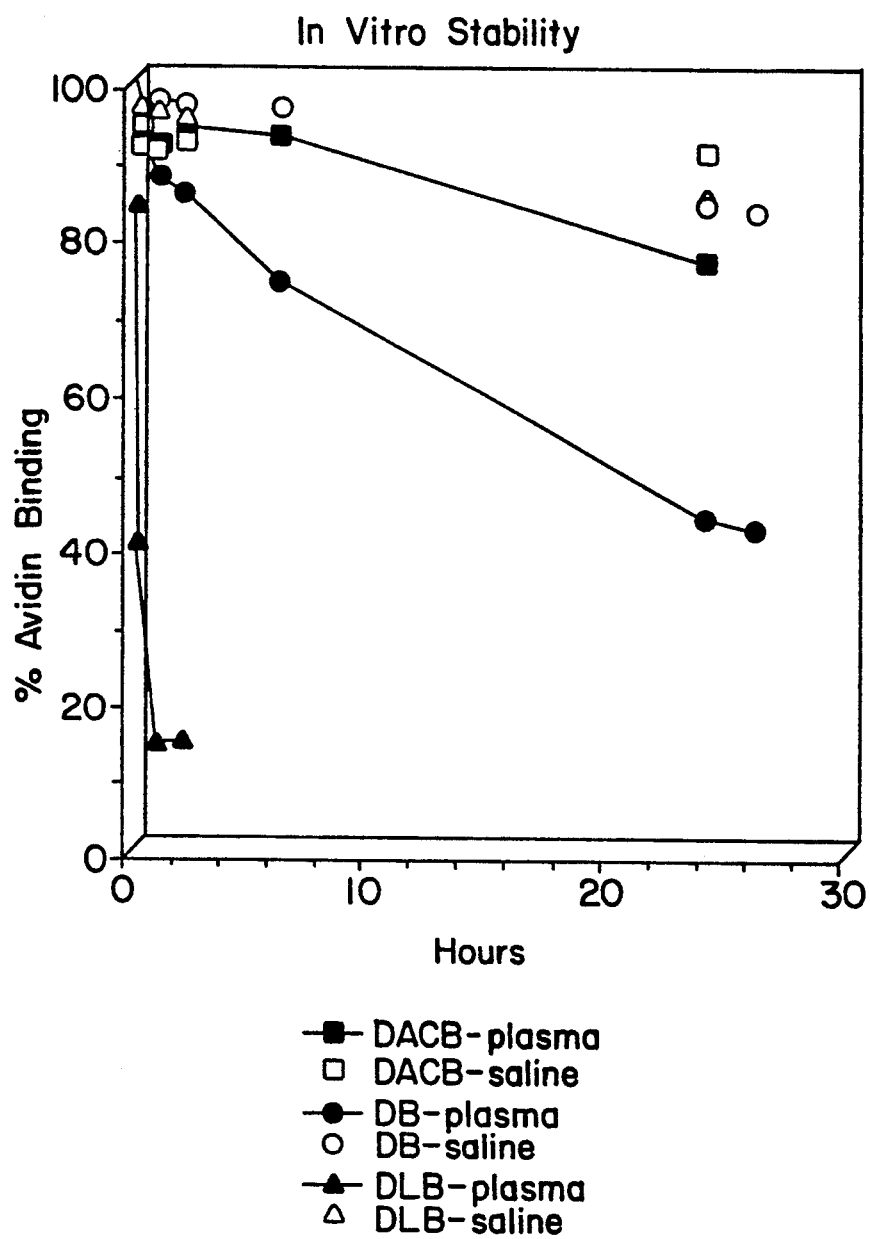
FIG. 1 is a graph of the percent of avidin binding ability retained in vitro by DACB, DB and DLB following incubation in saline and plasma.

The present invention is directed to compounds which are conjugates of biotin and deferoxamine which are stable in vivo, capable of binding metals ions with high affinity and stability, and capable of stably binding avidin and streptavidin. As used herein, conjugates which are "stable in vivo" are defined as those conjugates which maintain greater than 50% of both metal binding and avidin binding ability after incubation in The compounds of the present invention are provided by covalently bonding DFO and biotin or derivatives thereof and then assessing the resulting compounds for stability and activity, i.e. ability to chelate metal ions and bind avidin or streptavidin. Stability and activity can be evaluated in vitro by an avidin binding assay. In this assay, radioactive metal is bound to the DFO-biotin conjugate and the radioactive conjugate is incubated with avidin or streptavidin. Dissociation of the DFO-biotin conjugate is reflected as decreased radiometal bound to the biotin-avidin complex. Therefore, the integrity of the DFO-biotin conjugate, as well as its metal and avidin binding capability, can be assessed by measuring the amount of radioactivity which becomes associated with the avidin-biotin complex. Radio-active labeling of the DFO-biotin conjugate can be easily accomplished by direct addition of a radioactive metal solution, for example $^{67}$Ga, to the DFO-biotin conjugate, followed by incubation at room temperature for one to several hours. Avidin binding can be accomplished by incubating the radiolabeled DFO-biotin conjugate with an excess of avidin for a time sufficient for avidin-biotin binding (one to several minutes). This binding is most conveniently performed on a filter to effect subsequent separation of avidin and biotin from DFO and small metabolites. In a preferred embodiment, the filter is a Centricon 30 microfiltration device, which will retain avidin and DFO-biotin conjugates but not uncomplexed DFO or free radiometal. With a Centricon 30 filtration device, filtration is accomplished by centrifugation at about 4000-5000×g for about 20-30 minutes. The amount of radioisotope present in the incubation mixture is measured before and after filtration by methods well known to one of ordinary skill in the art and appropriate for the isotope used. For example, $^{67}$Ga is measured by a gamma counter. The ratio of radioactivity present in the unseparated incubation mixture to the radioactivity present in the retentate, i.e. the radioactivity bound to avidin via the DFO-biotin conjugate, provides a measurement of the stability of the DFO-biotin conjugate. For example, a ratio of 0.5 indicates that 50 percent of the radiolabeled conjugated has dissociated. The in vitro stability of the radiolabeled conjugates is assessed by performing the avidin binding assay after incubation of the conjugate in saline, or plasma for various amounts of time prior to the avidin binding assay.

To further assess the in vivo stability of the compounds of the present invention, the compounds can be radiolabeled and injected into animals. Plasma and urine samples are obtained at various time points and then subjected to the avidin binding assay described above to present at a concentration of about 2 mM. Specific methods for the separation and identification of DFO and its derivatives can be found in Kruck et al. [(1985) *J. Chromatogr.* 431, 123] and Singh et al. [(1990) *Anal. Biochem.* 187, 212].

It has been discovered in accordance with the present invention that a covalent conjugate of DFO and biotin, deferobiotin (DB), is stable in vivo, binds metals ions with high affinity and stability, and is capable of stably binding avidin and streptavidin. DB can be synthesized by covalently conjugating DFO and biotin, for example by the following Scheme II.

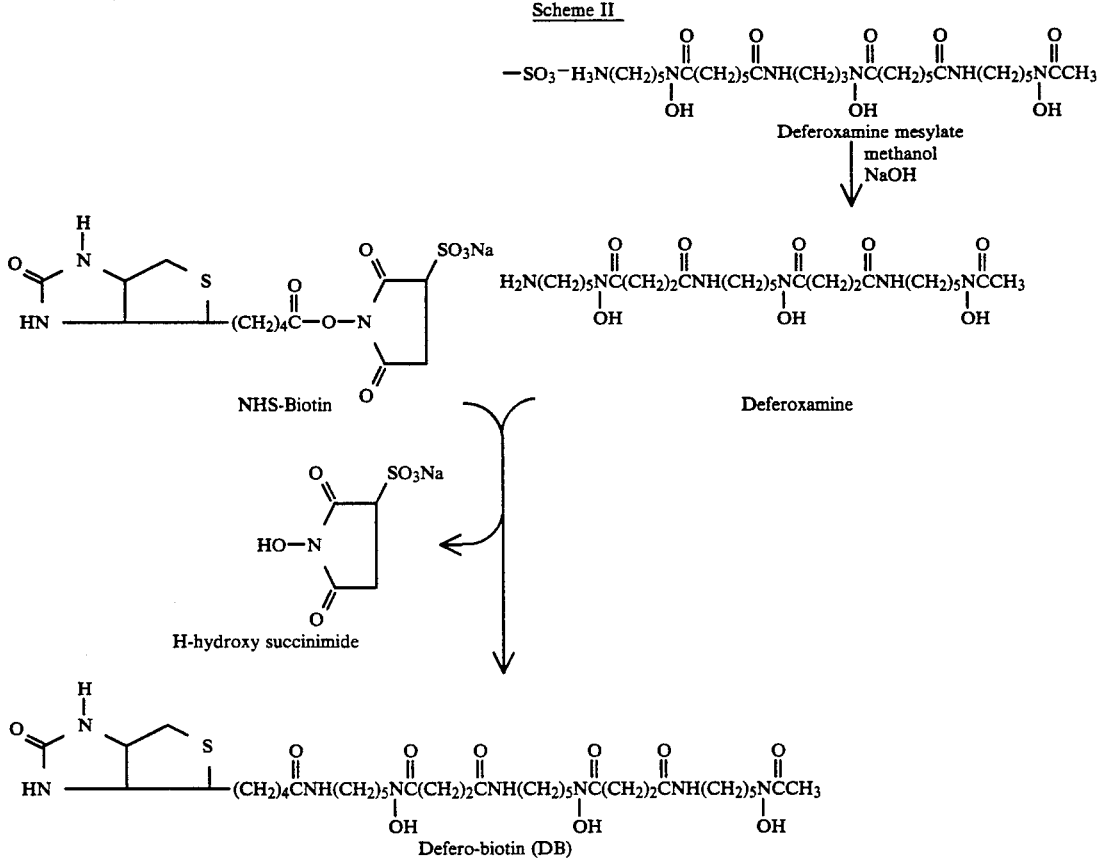

determine the amount of radioactivity which has remained associated with biotin, i.e. the stability of the DFO-biotin conjugate in vivo. Plasma and urine samples can also be analyzed, for example by high performance liquid chromatography (HPLC), to determine the presence of the intact DFO-biotin conjugate and its metabolites. The chromatographic profiles of plasma and urine samples can be compared to known profiles of unincubated radiolabeled DFO-biotin conjugates, unconjugated radiolabeled DFO, or other expected metabolites to determine whether the DFO-biotin conjugate has been degraded. Conditions and methods for HPLC are well known to one of ordinary skill in the art, and chromatographic conditions such as flow rate and gradient program can easily be selected and optimized by the skilled artisan. In a preferred embodiment, reverse phase chromatography is used and a complexing agent is included in the mobile phase to ensure that iron contamination present in buffers or bound to the column does not interfere with analysis. Preferably the complexing agent is nitrilotriacetic acid (NTA) and is The synthesis of DB according to Scheme II can be accomplished as follows. Solid deferoxamine mesylate is added to methanol for a concentration of about 10 mM, followed by addition of NaOH to reach a final concentration of 10 mM NaOH. The solution is maintained at about Solid NHS-biotin is added to the DFO solution to reach a final molarity of 20 mM NHS-biotin and incubated at least one hour at 60°. (Scheme II illustrates a water soluble analog of NHS-biotin, sulfo-NHS-biotin. One of ordinary skill in the art can determine appropriate biotin analogs which will react with the primary amine of DFO). The preferred molar ratio of NHS-biotin: deferoxamine mesylate is 2–5:1. DB synthesized according to Scheme II can be purified by standard methods known to the ordinarily skilled artisan, for example by HPLC.

The in vitro stability of DB can be determined by the avidin binding assay described hereinabove. DB is first labeled with radiometal. For example, DB can be labeled with $^{67}$Ga by direct addition of a $^{67}$Ga solution to DB, followed by incubation at room temperature for one to several hours, followed by incubation in saline or human plasma as described above. When $^{67}$Ga-DB is incubated at 37° in saline followed by measurement of avidin binding activity as described above, approximately 90% of the radiolabel maintains its ability to associate with avidin after twenty four hours, indicating that DB is extremely stable in saline. After incubation of $^{67}$Ga-DB in human plasma for six hours, approximately 75% of the radiolabel is capable of associating with avidin in the avidin binding assay, indicating that DB is also stable in plasma, and that DB does not undergo rapid degradation as does DLB.

The in vivo stability of DB can be evaluated by intravenously injecting radiolabeled DB, for example $^{67}$Ga-DB, into experimental animals such as dogs and then subjecting plasma and urine samples to the avidin binding assay as described above. This assay demonstrates that approximately 85% and 65% of the radioactivity present in urine and plasma samples, respectively, withdrawn at 60 minutes retains ability to bind avidin. This confirms the results of the in vitro studies and demonstrates that DB is stable in vivo and thus suitable for applications in in vivo imaging and therapy.

The stability of DB can be further evaluated by examining the plasma samples obtained in in vitro studies and urine samples obtained after intravenous injection of radiolabeled DB for the presence of DB, DFO and other possible metabolites, for example by HPLC. Specifically, radiolabeled DB is incubated in plasma for 24 hours and then subjected to chromatographic analysis by HPLC. The radioactivity in the column effluent is plotted as a function of the eluting solvent volume, and the HPLC elution profiles of unincubated radiolabeled DB and DFO are compared to radiolabeled DLB which has been incubated in plasma. The major peaks of radioactivity co-elute with unincubated DB and DFO, indicating that even after 24 hours, a considerable amount of DB remains intact.

Urine samples for HPLC analysis can be obtained by injecting radiolabeled DB into experimental animals such as dogs and obtaining urine samples by flushing the bladder at various time intervals. For example, urine samples are obtained at 30 minutes, 2 hours, and 4 hours and analyzed by HPLC. In samples obtained at 30 minutes, almost all of the radioactivity present co-elutes with the radioactivity in uninjected DB, whereas at 2 and 4 hours, increasing amounts of radioactivity co-elutes with radiolabeled DFO, indicating that DB is slowly dissociated in vivo to DFO and biotin.

In another preferred embodiment, a DFO-biotin conjugate is provided which is stable in vivo, binds metals ions with high affinity and stability, and is capable of stably binding avidin and streptavidin. This preferred compound, defero-acetyl-cysteinyl-biotin (DACB), contains an acetyl and cysteinyl group to provide the linkage between DFO and biotin. As discussed hereinabove, the nature of the linkage between DFO and biotin is of critical importance to minimize proteolysis by biotinidase and thus provide compounds which are stable in vivo.

DACB can be synthesized by covalently conjugating iodoacetyl-deferoxamine and N-cysteinyl-biotin, for example by the following Scheme III.

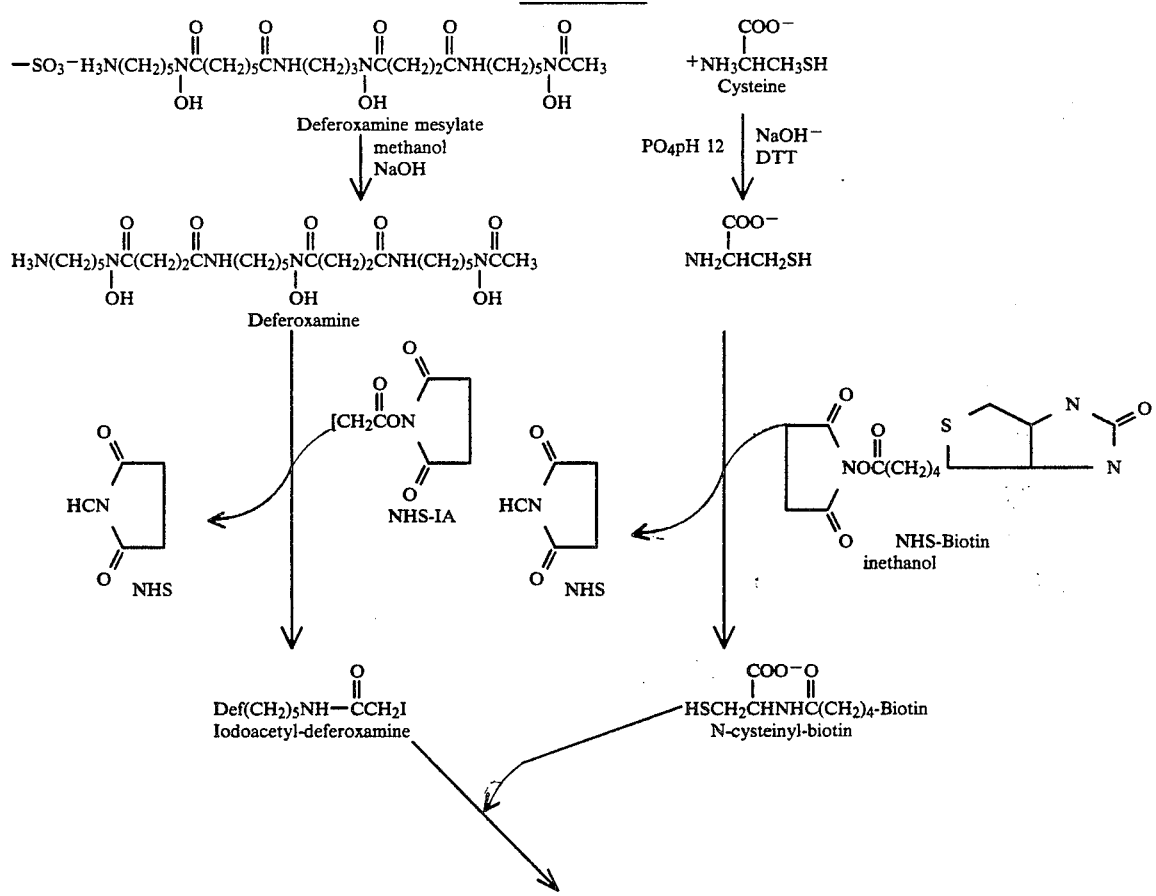

Scheme III

-continued
Scheme III

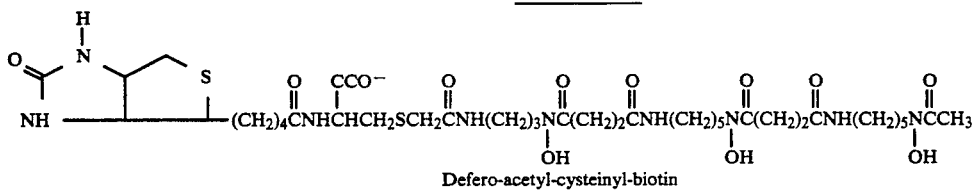

Defero-acetyl-cysteinyl-biotin

The synthesis of DACB by Scheme III can be accomplished as follows. Solid deferoxamine mesylate is added to methanol for a concentration of 20 mM, followed by addition of NaOH to reach a final concentration of 20 mM NaOH. The solution is heated and maintained at 65°. Solid iodoacetic acid N-hydroxysuccinimide ester (NHS-IA) is added to the deferoxamine solution to a final molarity of 50mM NHS-IA and incubated for at least one hour at 65°. The preferred molar ratio of NHS-IA:DFO is 2–10:1. The resulting iodoacetyl-deferoxamine (IA-DFO) is purified by HPLC, for example with an EM LiChroCART reverse phase column using a linear gradient of 0–10 ml 100% Buffer A (0.025M phosphate, pH 6, 2 mM NTA) and 10–60 ml 0–100% Buffer B (0.025M phosphate, pH 6, 2 mM NTA, 75% methanol). IA-DFO, but not unconjugated DFO, has an absorbance at 260nm and thus can be purified by measuring the absorbance of the eluate and collecting the fraction with absorbance at 260nm.

To prepare cysteinyl-biotin, cysteine is added to 0.05M phosphate buffer, pH 12 containing a concentration of dithiothreitol (DTT) at least equimolar to cysteine. For example, 60–120 mM DTT is added to cysteine in 0.05M phosphate buffer for a final concentration of 60 mM cysteine. NHS-biotin is solubilized in methanol at a concentration of 20 mM and heated to 60°. Equal volumes of the cysteine and NHS-biotin solutions are mixed and incubated at 65°. The preferred molar ratio of cysteine: NHS-biotin is 2–10:1. The resulting cys-biotin is purified, for example by HPLC. The fraction containing cys-biotin can be identified by its reactivity with 5,5'-dithiobis-(2-nitrobenzoic acid), (DTNB; Ellman's reagent). Ellman's reagent is used to detect thiols and reacts with cys-biotin but not with free biotin, which does not contain a free SH group.

The pH of purified cys-biotin and IA-DFO is adjusted to 7.5 with NaOH. Cys-biotin and IA-DFO are mixed and incubated overnight. The preferred molar ratio of cysbiotin:IA-DFO is 2:1. The resulting DACB is purified by standard methods known to one of ordinary skill in the art, for example by HPLC using the column and gradient parameters described above for the HPLC purification of IA-DFO.

To determine the in vitro stability of DACB, the avidin binding assay is used. DACB is first labeled with radiometal. For example, DACB can be labeled with $^{67}$Ga by direct addition of a $^{67}$Ga solution to DACB, followed by incubation at room temperature for one to several hours. Samples of radiolabeled DACB are added to 1 ml of saline or human plasma and then incubated at 37° for up to 24 hours. Aliquots of radiolabeled DACB are removed at various time points and tested for ability to bind avidin.

When $^{67}$Ga-DACB is incubated at 37° in saline followed by a measurement of avidin binding activity as described above, approximately 95% of the $^{67}$Ga retains its avidin binding ability after 24 hours of incubation, indicating that the conjugate is extremely stable in saline. It has been found that after incubation in human plasma for six hours, $^{67}$Ga-DACB binds to avidin at about 95% After 24 hours, approximately 80% of the radiolabel remains capable of associating with avidin in the avidin binding assay, indicating the excellent stability of DACB in plasma.

The in vivo stability of DACB can be evaluated by intravenously injecting radiolabeled DACB, for example $^{67}$Ga-DACB, into experimental animals such as dogs and then subjecting plasma and urine samples to the avidin binding assay as described above. This assay demonstrates that approximately 95% and 85% of the radioactivity present in urine and plasma samples, respectively, withdrawn at 60 minutes retains ability to bind avidin. This confirms the results of the in vitro studies and demonstrates that DACB is extremely stable in vivo and thus suitable for applications in in vivo imaging and therapy.

The stability of DACB can be further evaluated by examining the urine samples obtained after intravenous injection of radiolabeled DB for the presence of DB, DFO and other possible metabolites, for example by HPLC. Urine samples for HPLC analysis can be obtained by injecting radiolabeled DACB into experimental animals such as dogs and obtaining urine samples by flushing the bladder at various time intervals. For example, urine samples are obtained at 30 minutes, 2 hours, and 4 hours and analyzed by HPLC. The radioactivity in the column effluent is plotted as a function of the eluting solvent volume, and the HPLC elution profiles of uninjected radiolabeled DACB and DFO are compared to radiolabeled DACB in urine samples. In samples obtained at 30 minutes, all of the radioactivity present co-elutes with the radioactivity in uninjected DACB, confirming that DACB has excellent stability in vivo.

Another aspect of the present invention provides the subject DFO-biotin conjugates labeled with a metal ion. In a preferred embodiment, the metal is paramagnetic or radioactive. As discussed hereinabove, the amine group of DFO involved in conjugation with biotin or biotin derivatives is spatially separated from the hydroxamic groups which comprise the metal chelating moiety, and therefore conjugation of DFO does not compromise chelating ability. Accordingly, all metals capable of forming stable metal chelates with DFO are contemplated as useful for labeling the compounds of the present invention. In a preferred embodiment, the DFO-biotin conjugates of the present invention are labeled by chelation with Fe, Gd, $^{99m}$Tc, $^{111}$In, $^{67}$Ga, $^{90}$Y, $^{186}$Re, $^{188}$Re, or $^{212}$Bi. Chelation with metal ions can be accomplished by methods known to one of ordinary skill in the art. For example, the compounds of the present invention can be labeled with $^{67}$Ga by direct addition of a $^{67}$Ga solution to the DFO-biotin conjugate, followed by incubation at room temperature for one to several hours.

Another aspect of the present invention is directed to a method of immunoimaging or immunotherapy using the subject labeled DFO-biotin compounds as a delivery system for radioactive, paramagnetic or other metals with therapeutic use.

The two-step approach comprises administering an avidin or streptavidin conjugated monoclonal antibody (MAb) specific for a tissue or lesion of interest to a patient, followed by administering, one to several days later, the DFO-biotin conjugate of the present invention which has been labeled with a paramagnetic or radioactive metal. For radioimmunoimaging of the tissue or lesion of interest, it is preferred that the DFO-biotin conjugate is labeled with Fe, Gd, $^{52}$Fe, $^{68}$Ga, $^{99m}$Tc, $^{111}$In, or $^{67}$Ga. For radioimmunotherapy, it is preferred that the DFO-biotin conjugate is labeled with $^{186}$Re, $^{188}$Re, $^{212}$Bi or $^{90}$Y. In radioimmunoimaging applications, administration of the labeled DFO-biotin conjugate is followed by detection of the complex. The method used for diagnostic imaging is appropriate for the particular metal in the conjugate. For example, paramagnetic metal ions such as Fe and Gd are suitable for nuclear magnetic resonance (NMR) analysis or magnetic resonance imaging (MRI). $^{52}$Fe and $^{68}$Ga are appropriate for analysis by positron emission tomography (PET), whereas $^{99m}$Tc, $^{111}$In and $^{67}$Ga can be detected by gamma camera imaging. The aforementioned means of image analysis are known to one of ordinary skill in the art and can be conducted in accordance with well-established techniques.

The two-step radioimmunoimaging and radioimmunotherapy methods described above utilize avidin or streptavidin conjugated monoclonal antibodies. Antibodies contemplated by the present invention include anti-tumor antibodies, anti-fibrin antibodies, anti-myosin antibodies and any lesion-specific antibodies. Anti-fibrin and antimyosin antibodies are particularly useful in cardiac imaging. Non-specific lgG is also useful in accordance with the present invention since it can be used in targeting of abscesses via Fc receptor binding. Standard methods for the production and purification of MAbs are known to one of ordinary skill in the art and can be found, for example, in *Antibodies: A Laboratory Manual*, Harlow et al., eds, (1988) Cold Spring Harbor Laboratory. Methods for conjugating avidin or streptavidin to monoclonal antibodies are known to one of ordinary skill in the art. For example, Kalofonos et al. (1990) and Hnatowich et al. (1987) disclose methods for conjugating an antibody with streptavidin and avidin, respectively, which use biotin as a linking group between the antibody and streptavidin or avidin.

In another embodiment of the present invention, the target-specific antibody and DFO-biotin conjugate are administered to the host as a pharmaceutical composition in an amount sufficient for the desired therapeutic or diagnostic effect. The pharmaceutical compositions contain an effective dosage of the conjugates according to the present invention together with a pharmaceutically acceptable carrier. The compounds can be administered by well-known routes including oral, intravenous, intramuscular, intranasal, intradermal, subcutaneous, parenteral and the like. Depending on the route of administration, the pharmaceutical compositions may require protective coatings.

The pharmaceutical forms suitable for injectionable use include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water, buffered aqueous solutions (i.e., biocompatible buffers), ethanol, polyol (glycerol, propylene glycol, polyethylene glycol and the like), suitable mixtures thereof, surfactants or vegetable oils. Sterilization can be accomplished by any art recognized technique, including but not limited to, addition of antibacterial or antifungal agents, for example, paraben, chlorobutanol, phenol, sorbic acid, thimerosal, and the like. Further, isotonic agents, such as sugars or sodium chloride may be incorporated in the subject compositions.

Production of sterile injectable solutions containing the subject contrast agent is accomplished by incorporating these agents in the required amount in the appropriate solvent with various ingredients enumerated above, as required, followed by sterilization, preferably filter sterilization. To obtain a sterile powder, the above solutions are vacuum-dried or freeze-dried as necessary.

When the conjugates are administered orally, the pharmaceutical composition thereof containing an effective dosage of the contrast agent, may also contain an inert diluent, an assimilable edible carrier and the like, be in hard or soft shell gelatin capsules, be compressed into tablets, or may be in an elixir, suspension, syrup or the like. Preferred compositions of the conjugated antibody provide effective dosages in the range of about 0.1–5 mg. In a preferred embodiment the effective dosage is about 1 mg. Preferred compositions of the labeled DFO-biotin conjugate provide effective dosages in the range of about 1–1000 µg. The preferred dosage range of labeled DFO-biotin is about 10–100 µg.

As used herein, a pharmaceutically acceptable carrier includes any and all solvents, dispersion media, coatings, antibacterial and antifungal agents, isotonic agents, and the like. The use of such media and agents are well-known in the art.

The present invention is also directed to a kit for radioimaging or radiotherapy. In one embodiment, the kit is compartmentalized to receive a container adapted to contain a DFO-biotin conjugate of the present invention. In an exemplified use of the subject kit, the DFO-biotin conjugate is labeled with a radioactive or paramagnetic metal and administered to a patient one to several days after administration of streptavidin or avidin-conjugated targeting agent.

In another embodiment, the kit is compartmentalized to receive a first container adapted to contain a DFO-biotin conjugate of the present invention, and a second container adapted to contain an avidin or streptavidin conjugated antigen-, cell- or tissue-specific targeting agent. In an exemplified use of the subject kit, the contents of the second container are administered to a host. The DFO-biotin conjugate is labeled with a radioactive or paramagnetic metal and administered to the host one to several days after the administration of the targeting agent. In a preferred embodiment, the DFO-biotin conjugate is DB or DACB.

The following examples further illustrate the invention.

EXAMPLE I

Synthesis and Analysis of Defero-desaminolysyl-biotin

Biocytin was covalently linked to DFO by the following Scheme I, in which DFO was provided as its commercially available form, deferoxamine mesylate.

Scheme I results in the synthesis of DLB, a covalent conjugate of DFO and biotin.

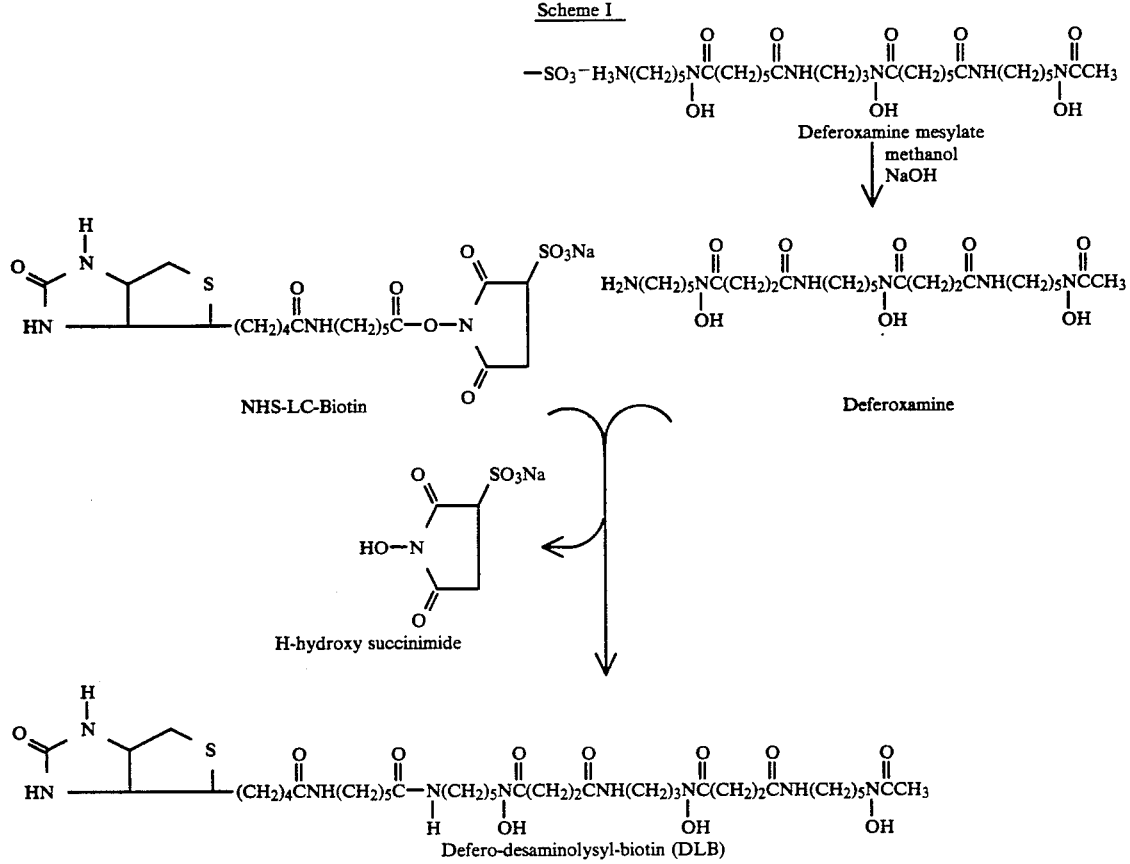

The synthesis of DLB according to Scheme 1 was accomplished as follows. Solid deferoxamine mesylate was added to methanol for a concentration of about 10 mM, followed by addition of NaOH to reach a final concentration of 10 mM NaOH. The solution was maintained at about 60°. Solid NHS-LC-biotin was added to the deferoxamine solution to reach a final molarity of 20 mM NHS-LC-biotin and incubated at least one hour at 60°. The preferred molar ratio of NHS-LC-biotin: deferoxamine mesylate is 2–5:1. DLB synthesized according to Scheme I was purified by standard methods known to the ordinarily skilled artisan, for example high performance liquid chromatography (HPLC).

To determine the in vitro stability of DLB, the avidin binding assay was used. DLB was labeled with $^{67}Ga$ by direct addition of a $^{67}Ga$ solution to DLB, followed by incubation at room temperature for one to several hours. Samples of radiolabeled DLB were added to 1 ml of saline or human plasma and then incubated at 37° for up to 24 hours. Aliquots of radiolabeled DLB were removed at various time points and tested for ability to bind avidin.

As shown in FIG. 1, when $^{67}Ga$-DLB was incubated at 37° in saline followed by a measurement of avidin binding activity as described above, approximately 85% of the $^{67}Ga$ retained its avidin binding ability after 24 hours of incubation, indicating that the conjugate is stable in saline. It has been surprising found that after incubation in human plasma, $^{67}Ga$-DLB rapidly lost its avidin binding ability, with less than 50% of the radiolabel capable of binding avidin after 10 minutes of incubation in plasma, and less than 15% at 2 hours, demonstrating that the conjugate was rapidly dissociating under physiological conditions.

Figure 3:
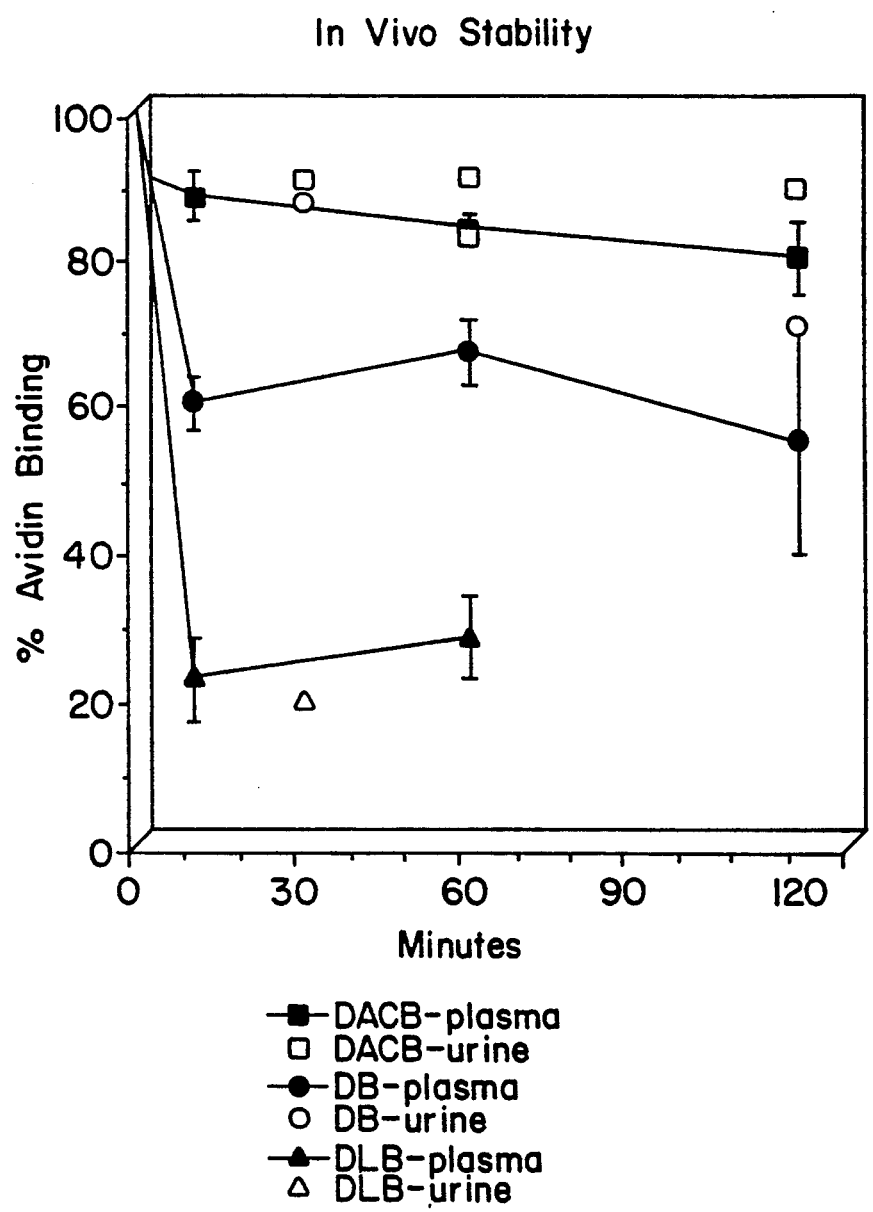
FIG. 3 is a graph of the percent of avidin binding ability retained by DACB, DB and DLB in plasma and urine samples following intravenous injection of the conjugates.

The in vivo stability of DLB was further assessed by intravenously injecting $^{67}Ga$-DLB, into dogs and then subjecting plasma and urine samples to the avidin binding assay. Blood was withdrawn at intervals after injection of $^{67}Ga$-DLB and dispensed into heparinized tubes for plasma analysis. Urine samples were obtained by flushing the bladder with saline approximately every thirty minutes. Avidin binding assays of the plasma and urine samples indicate that only about 20% of the radioactivity present in plasma and urine samples withdrawn at ten and thirty minutes, respectively, retained its ability to bind avidin. These results are shown in FIG. 3. This confirms results of in vitro studies and demonstrates that DLB is unstable in vivo.

Figure 2:
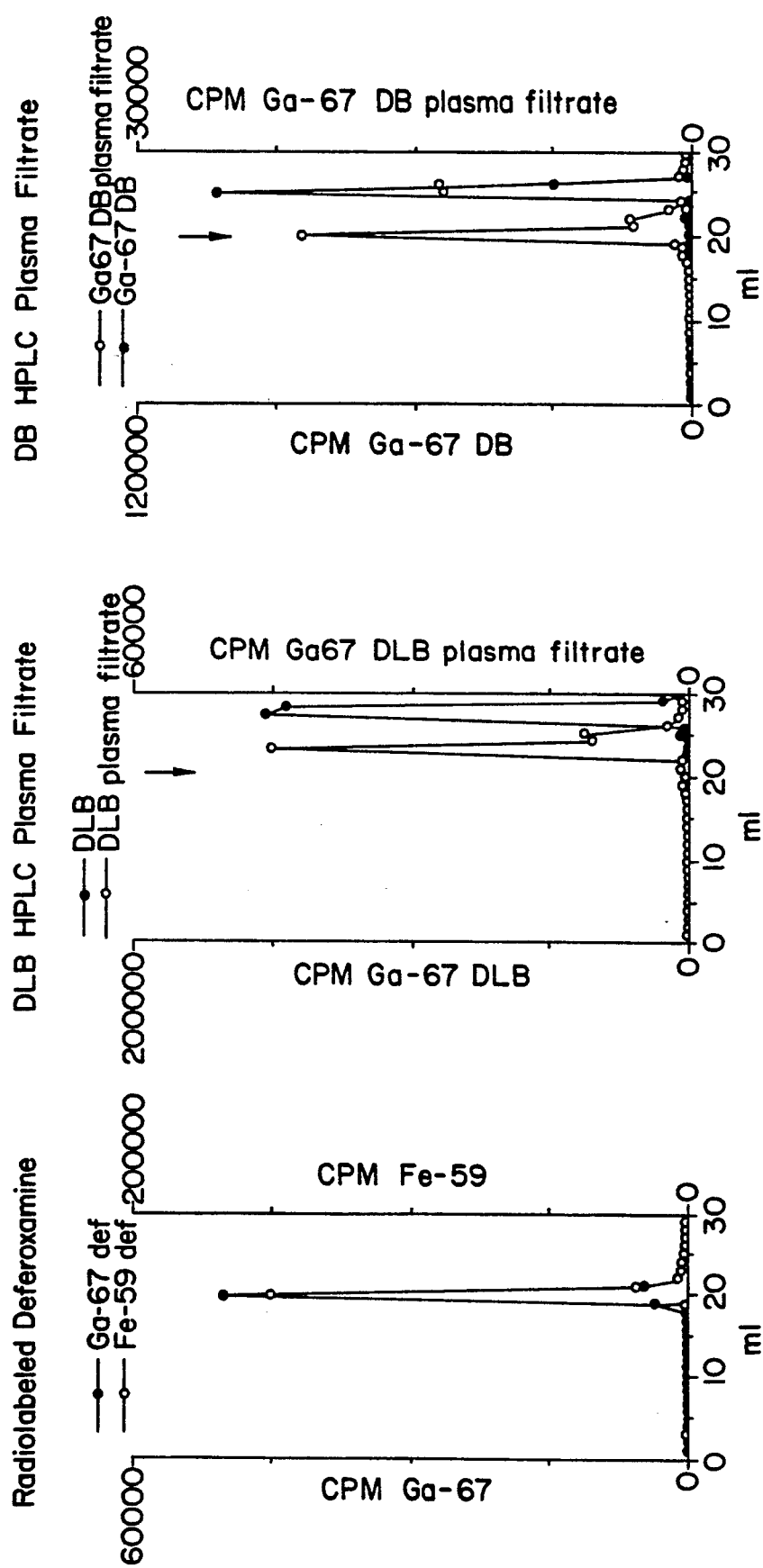
FIGS. 2A-2C present HPLC profiles of radiolabeled DFO (FIG. 2A), DB (FIG. 2C) and DLB (FIG. 2B) following incubation in plasma. The radioactivity in the column effluent is plotted as a function of the eluting solvent volume.

To further assess the stability of DLB, $^{67}Ga$-DLB was incubated in plasma at 37° for two hours and then subjected to chromatographic analysis by HPLC. The radioactivity in the column effluent was plotted as a function of the eluting solvent volume, and the HPLC elution profiles of unincubated radiolabeled DLB and DFO were compared to radiolabeled DLB which had been incubated in plasma. The chromatographic profile is depicted in FIG. 2. The major peak of radioactivity in the plasma-incubated sample eluted earlier than the major peak of the unincubated sample, indicating that DLB is unstable. However, the plasma-incubated sample did not co-elute with radiolabeled DFO, indicating that DLB had not simply dissociated into DFO and biocytin, but rather demonstrates that DLB was rapidly degraded in vivo to biotin and desaminolysyl-deferoxamine. Chromatographic analysis of urine samples from the in vivo experiments described above and shown in FIG. 4, confirms that, even after thirty minutes, radiolabeled DLB had been degraded to desaminolysyl-deferoxamine.

EXAMPLE II

In Vitro Stability of DLB, DB and DACB

DLB, DB and DACB were each labeled with $^{67}$Ga by direct addition of a $^{67}$Ga citrate solution (specific activity of 50–500 $\mu$Ci/$\mu$g of $^{67}$Ga) followed by incubation overnight at room temperature. Samples of each radiolabeled conjugate were added to 1 ml of saline and 1 ml of dog plasma and incubated at 37° C. for 26 hours. 100 $\mu$l aliquots of the radiolabeled conjugates were removed at various time points and assessed by the avidin binding assay.

Each radiolabeled conjugate was incubated with 100 $\mu$g avidin for 1–10 minutes at room temperature on a centricon 30 filter. Filters were counted in a gamma counter, washed with PBS, pH 7.5, and centrifuged at 4000–5000g for 20 minutes for saline samples and 30 minutes for plasma samples. After washing/centrifugation, filters were again counted. The ratio of counts per minute (cpm) after centrifugation to before centrifugation was calculated. A ratio of 1 represents 100% avidin binding ability retained after incubation. Results are plotted as percent avidin binding ability per unit time and shown in FIG. 1.

Plasma filtrates of DLB and DB were analyzed by HPLC and compared to the HPLC profiles of $^{67}$Ga- and $^{59}$Fe-labeled DFO. Results are shown in FIG. 2. The profiles of $^{67}$Ga-DFO and $^{59}$Fe-DFO, which are identical, are shown in Panel A and indicated by the arrows in Panels B and C.

EXAMPLE III

In Vivo Stability of DLB, DB and DACB

Figure 4:
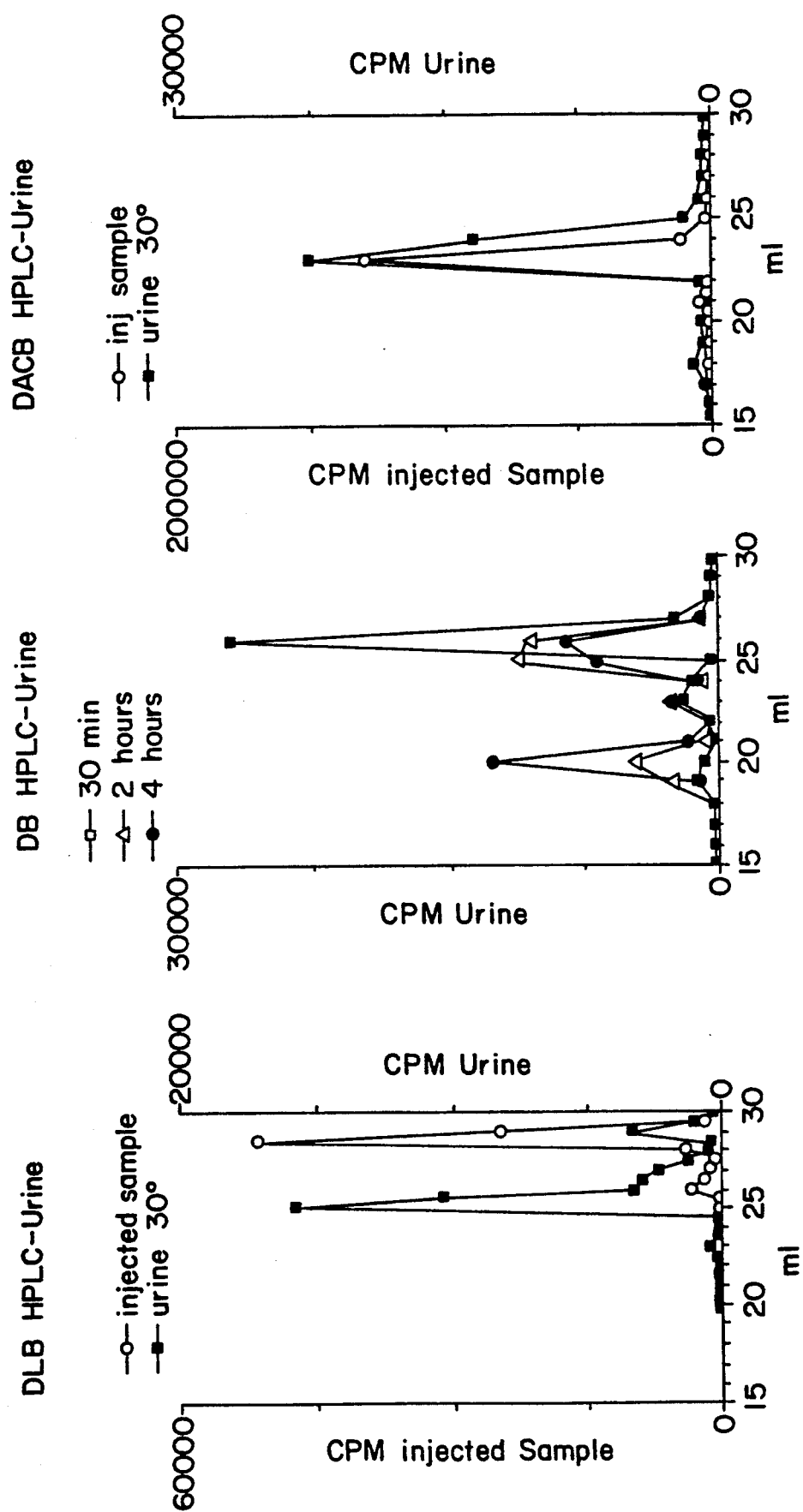
FIG. 4A present HPLC profiles of urine samples obtained after intravenous injection of radiolabeled DLB, (FIG. 4A) DB (FIG. 4B) and DACB (FIG. 4C).

DLB, DB and DACB were labeled with $^{67}$Ga as described in Example 1 and counted in a gamma counter. Each radiolabeled compound (1.2 $\mu$g DLB, 5 $\mu$g DB or 5 $\mu$g DACB) was intravenously injected into a dog. Whole blood was taken at 10, 60 and 120 minutes after injection and dispensed into heparinized tubes. Urine samples were obtained by flushing the bladder with 100 ml saline at 30, 60 and 120 minutes. Avidin binding was assessed and graphed as described in Example I. Results are shown in FIG. 3. Urine samples obtained 30 minutes, 2 hours and 4 hours after radiolabeled DB injection, and 30 minutes after radiolabeled DACB injection were analyzed by HPLC as described in Example I and compared to the HPLC profiles of the labeled compounds before injection. Results are depicted in FIG. 4.

EXAMPLE IV

Avidin Binding Ratio of $^{67}$Ga-DLB

The ratio of moles of radiolabeled DFO-biotin bound per mole of avidin ("bound ratio") was determined and compared to the bound ratio of commercially available DTPA-biotin.

Figure 5:
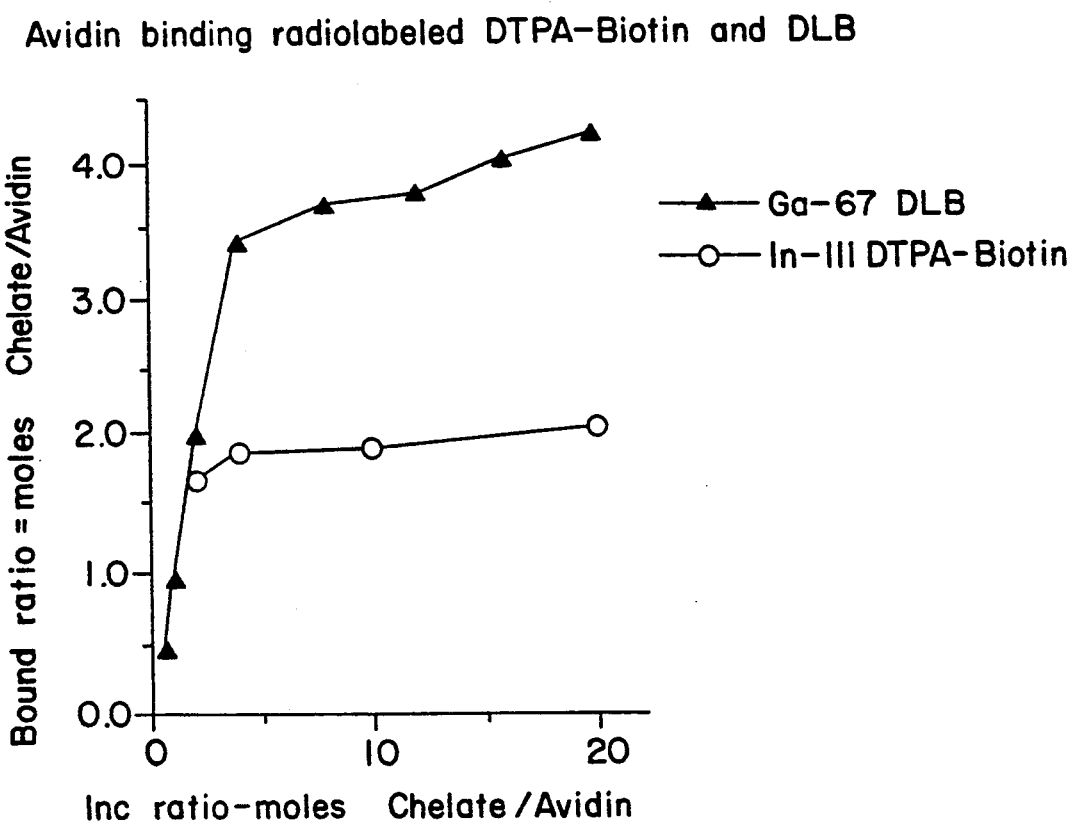
FIG. 5 is a graph demonstrating the bound ratio of $^{67}$Ga-DLB and $^{111}$In-DTPA-biotin bound to avidin.

As demonstrated in FIG. 5, the bound ratio for $^{67}$Ga-DLB approached 4, as compared to 2 for $^{111}$In-DTPA-biotin. These results indicate that radiolabeled DFO-biotin is capable of delivering twice as much label to a SA-or avidin-conjugated MAb compared to DTPA-biotin.

These results further indicate that one mole of DTPA-biotin probably fills 2 binding sites on avidin (avidin has four binding sites for biotin).

Figure 6:
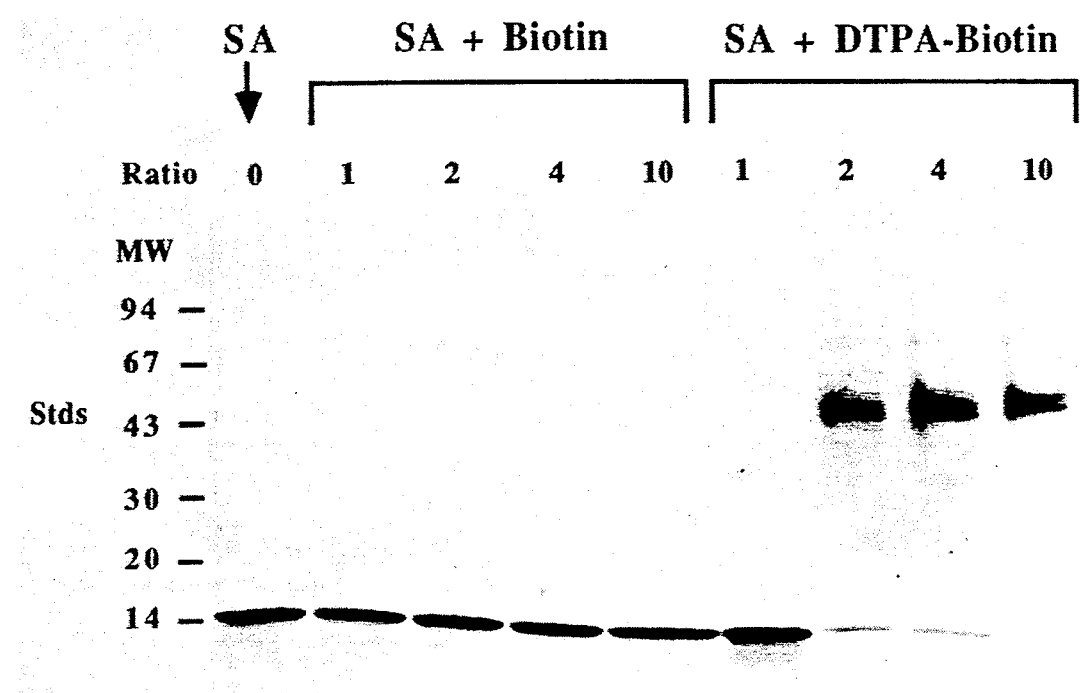
FIG. 6 depicts the electrophoretic migration of SA following incubation with increasing molar ratios of biotin and DTPA-biotin.

Electrophoretic analysis, as shown in FIG. 6, confirms that at a molar ratio of 2 or more, DTPA-biotin stabilizes SA by binding and bridging the binding sites. When SA is incubated with biotin and subjected to electrophoresis, SA migrates at its subunit molecular weight. When incubated with DTPA-biotin at a molar ratio of 2 or more, SA migrates at approximately 60 KD, indicating that the 4 moles of biotin present in 2 moles of DTPA-biotin are bridging SA via its 4 biotin binding sites.

EXAMPLE V

Pharmacokinetics of $^{67}$Ga-DACB

The basic in vivo pharmacokinetic parameters of $^{67}$Ga-DACB were examined as follows.

$^{67}$Ga-DACB was intravenously injected to dogs at a dose of 5 $\mu$g and the blood clearance and urinary excretion monitored. Whole blood was taken at intervals after iv injection placed in pre-weighed tubes. The pharmacokinetics were determined using the R-Strip curve fitting program (Micromath, Salt Lake City, Utah). Blood was also dispensed into heparinized tubes for plasma analysis. To determine urinary excretion of $^{67}$Ga-DACB in the dog, the bladder was flushed with approximately 30 ml of saline every 30 minutes. Total accumulated radioactivity per time increment (30 minutes) was determined by multiplying sample counts by the total volume of urine collected.

As indicated in FIG. 7, Panel A, the plasma pharmacokinetics of DACB are best fit by a three exponential fit, typical of small radioactive chelates. As indicated in FIG. 7, Panel B, at 100 minutes after injection, 50% of DACB had accumulated in the urine, while at 6 hours 80% of DACB had accumulated in the urine.

We claim:

1. A compound having the formula

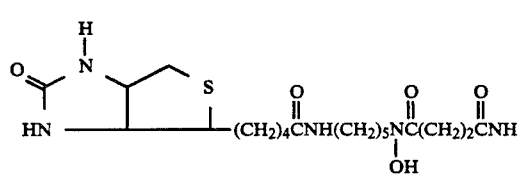

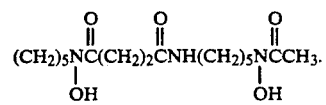

2. A compound having the formula

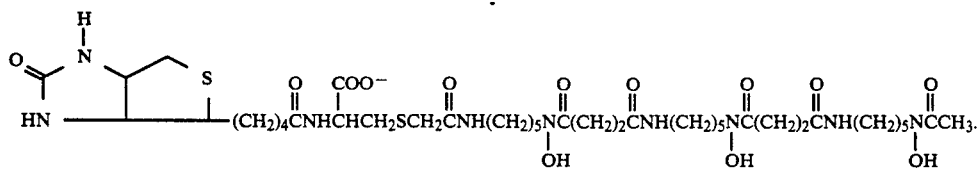

3. A pharmaceutical composition comprising a compound having the formula

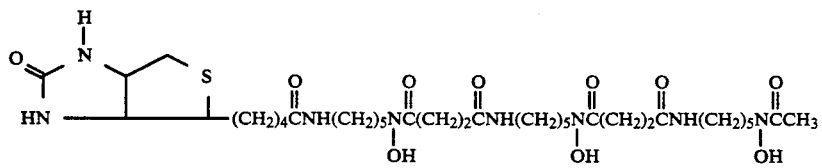

and a pharmaceutically acceptable carrier.

4. A pharmaceutical composition comprising a compound having the formula

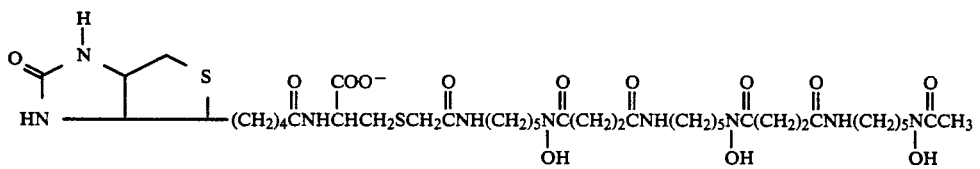

and a pharmaceutically acceptable carrier.

5. The pharmaceutical composition of claim 3 or 4 wherein said compound is present at a unit dosage of about 1–1000 μg.

6. The pharmaceutical composition of claim 1 wherein said compound is present at a unit dosage of about 10–100 μg.

7. A compartmentalized kit for radioimaging or radiotherapy comprising a container adapted to contain the compound of claim 1.

8. A compartmentalized kit for radioimaging or radiotherapy comprising a container adapted to contain the compound of claim 2.

9. A compartmentalized kit for radioimaging or radiotherapy comprising a first container adapted to contain a deferoxamine-biotin conjugate having the formula

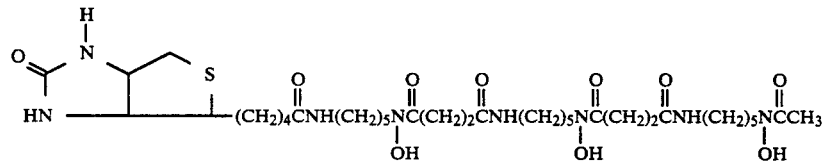

and a second container adapted to contain an avidin- or streptavidin-conjugated targeting agent.

10. A compartmentalized kit for radioimaging or radiotherapy comprising a first container adapted to contain a deferoxamine-biotin conjugate having the formula

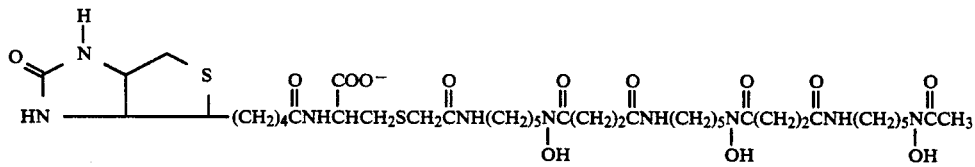

and a second container adapted to contain an avidin- or streptavidin-conjugated targeting agent.

11. The kit according to claim 9 wherein said targeting agent is a monoclonal antibody.

12. The kit according to claim 10 wherein said targeting agent is a monoclonal antibody.

* * * * *

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

Column 1, line 68: "$(K_a=10^{-15})$" should read --$(K_d=10^{-15})$--

Column 2, line 24: "streptavidinbiotin" should read --streptavidin-biotin--

Column 4, line 19: "$^{18}Re$" should read --$^{188}Re$--

Column 5, line 52:

"

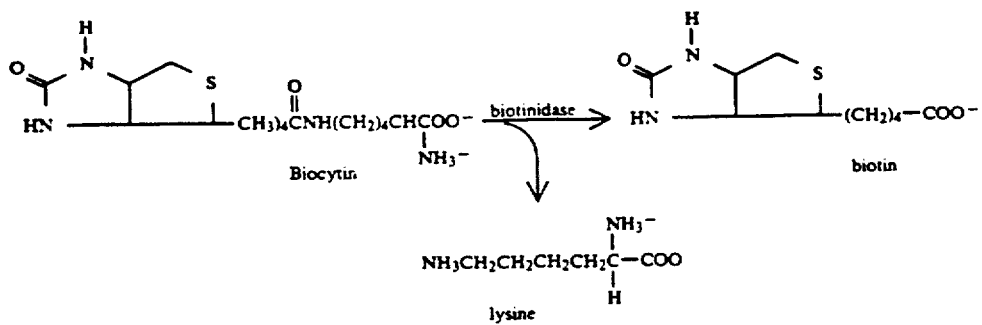

"

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

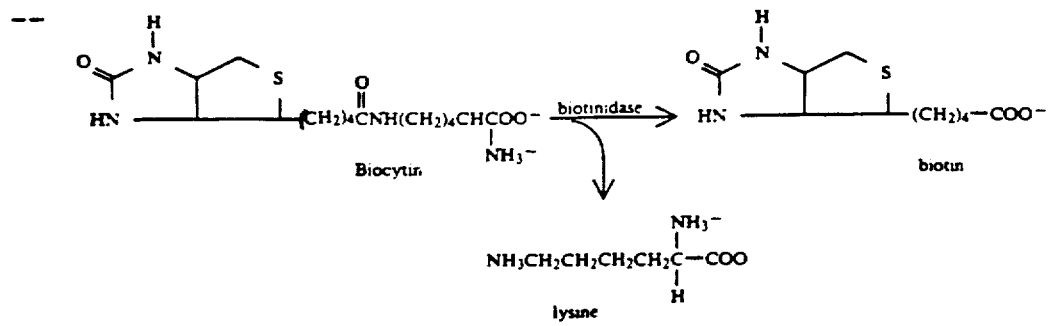

Column 5, line 65: before "specific delete --.--
Column 6, line 9: delete "o"
Column 6, line 33:

"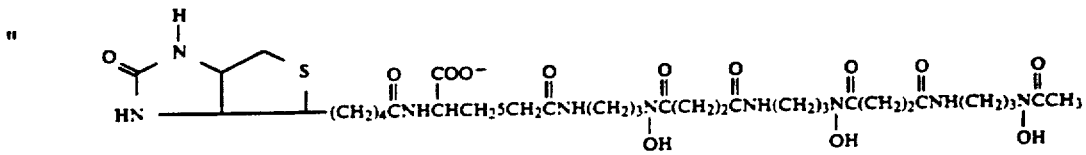"

should read

--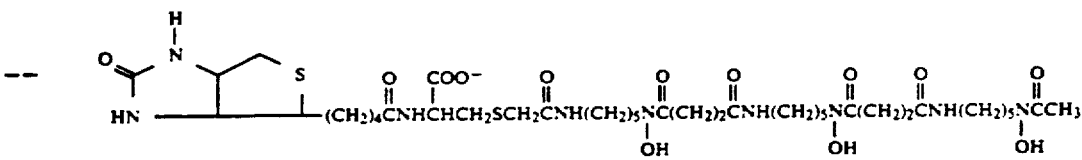--

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

Column 7, line 47: "FIG. 4A" should read --FIGS. 4A-4C--

Column 7, line 63: "metals ions" should read --metal ions--

Column 8, line 11:

" 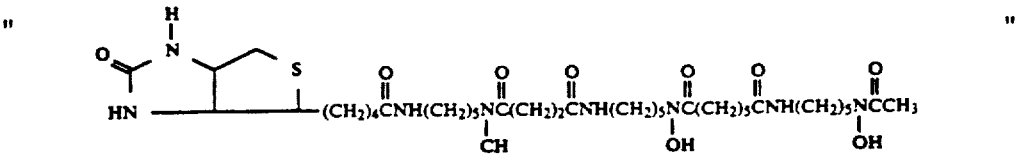 "

should read

-- 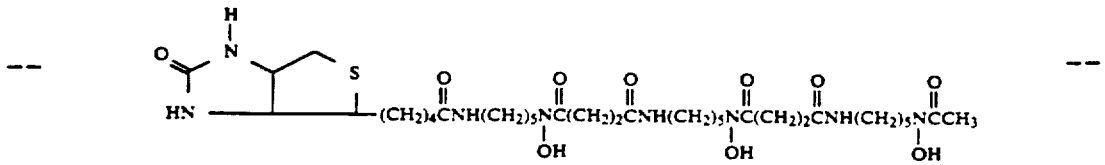 --

UNITED STATES PATENT AND TRADEMARK OFFICE
CERTIFICATE OF CORRECTION

PATENT NO. : 5,326,778  
DATED : July 5, 1994  
INVENTOR(S) : Scott F. Rosebrough Page 4 of 10

It is certified that error appears in the above-indentified patent and that said Letters Patent is hereby corrected as shown below:

Column 8, line 23:

"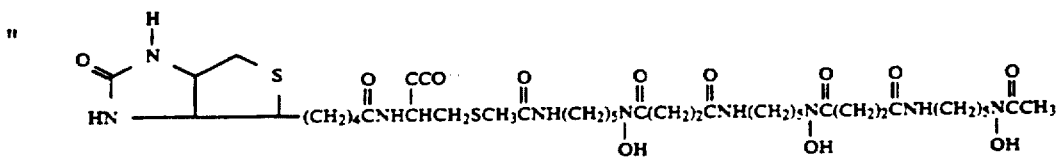"

should read

--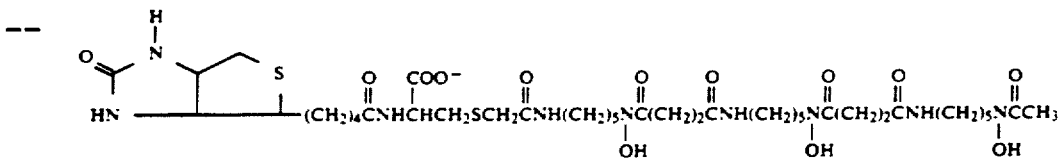--

Column 10, line 15:

"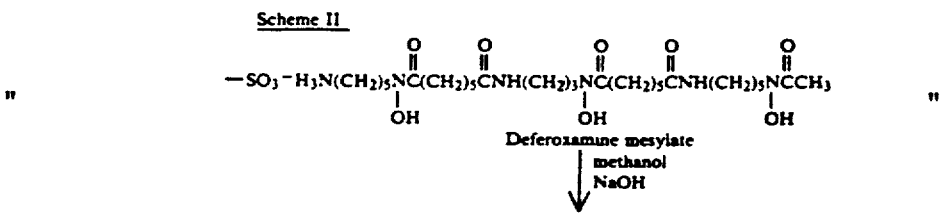"

UNITED STATES PATENT AND TRADEMARK OFFICE
CERTIFICATE OF CORRECTION

PATENT NO. : 5,326,778

DATED : July 5, 1994

INVENTOR(S) : Scott F. Rosebrough

It is certified that error appears in the above-indentified patent and that said Letters Patent is hereby corrected as shown below:

" should read "

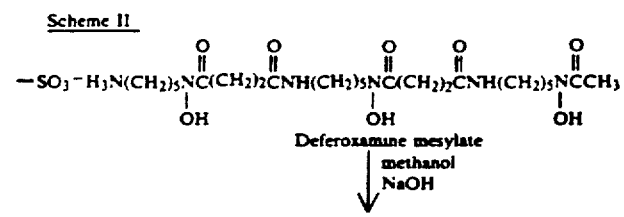

Column 10, line 54: after "about" insert --60°--

Column 12, lines 21-22: "metals ions" should read --metal ions--

UNITED STATES PATENT AND TRADEMARK OFFICE
CERTIFICATE OF CORRECTION

PATENT NO. : 5,326,778

DATED : July 5, 1994

INVENTOR(S) : Scott F. Rosebrough

It is certified that error appears in the above-indentified patent and that said Letters Patent is hereby corrected as shown below:

Column 12, line 34:

"
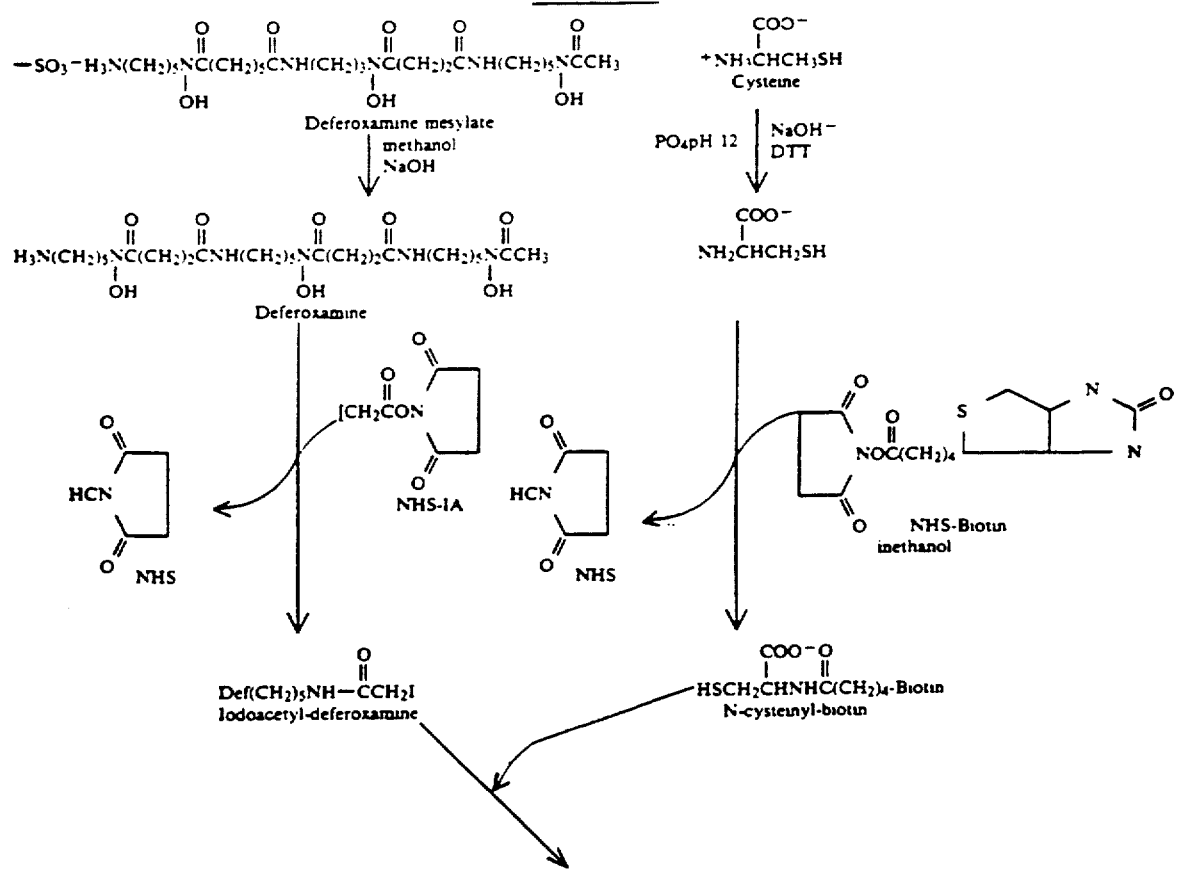
"

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

should read

"

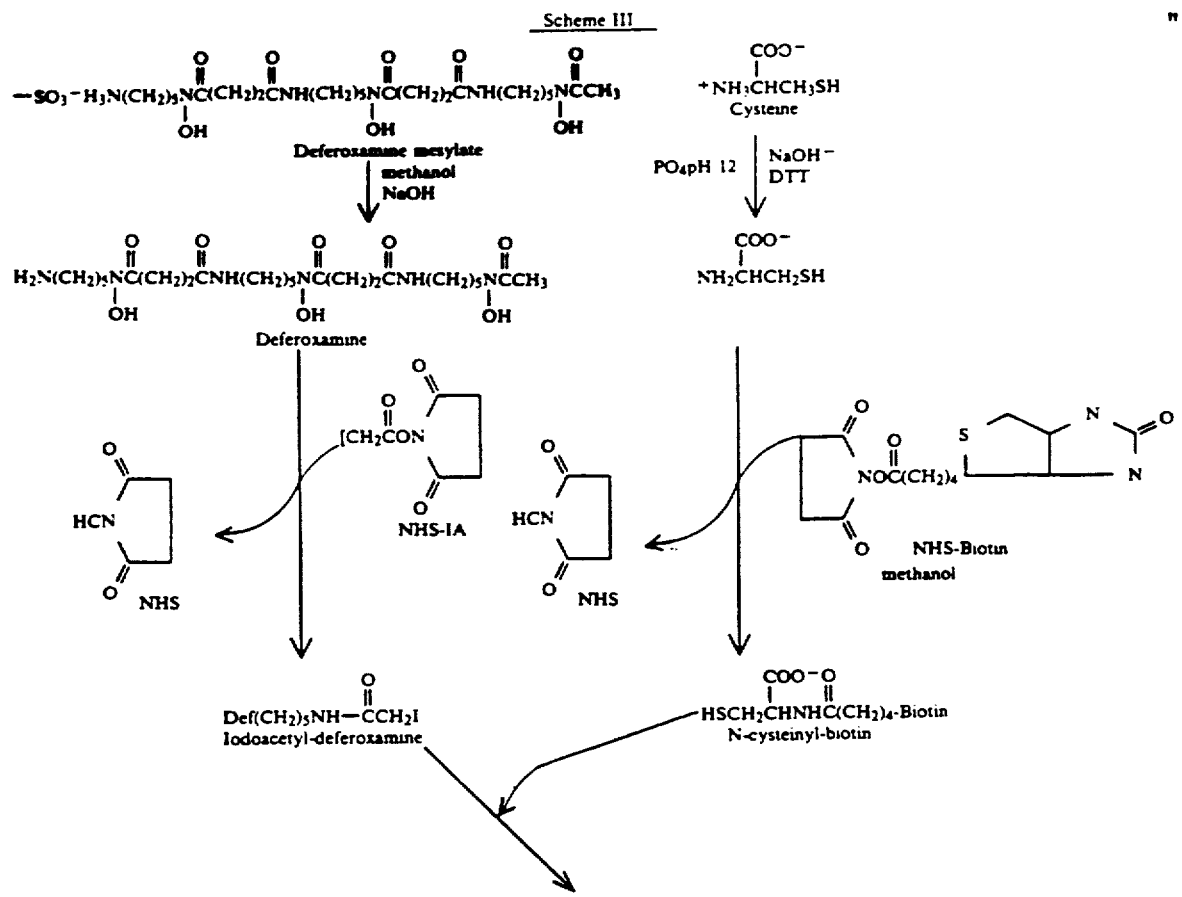

"

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

Column 13, line 6:

" 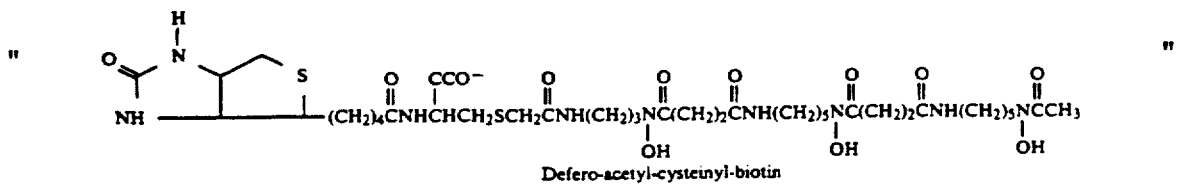 "

should read

-- 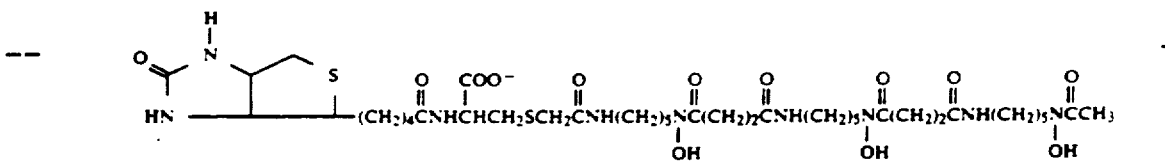 --

Column 13, line 49: "cysbiotin" should read --cys-biotin--

Column 14, line 14: after "95%" insert --.--

UNITED STATES PATENT AND TRADEMARK OFFICE
CERTIFICATE OF CORRECTION

PATENT NO. : 5,326,778

DATED : July 5, 1994

INVENTOR(S) : Scott F. Rosebrough

Page 9 of 10

It is certified that error appears in the above-indentified patent and that said Letters Patent is hereby corrected as shown below:

Column 18, line 6:

" 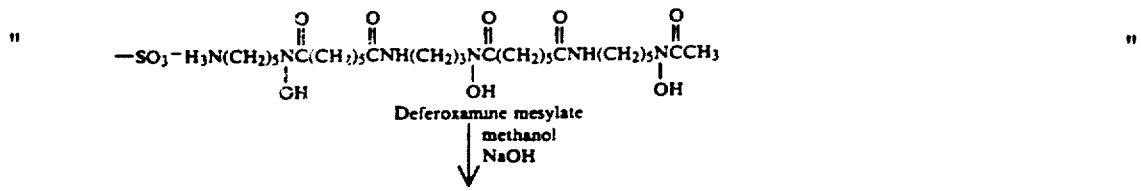 "

should read

-- 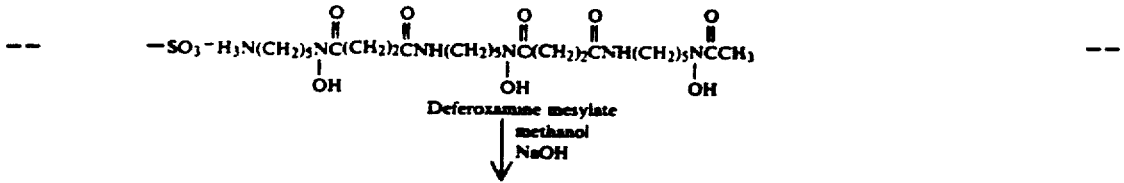 --

UNITED STATES PATENT AND TRADEMARK OFFICE
CERTIFICATE OF CORRECTION

PATENT NO. : 5,326,778
DATED : July 5, 1996
INVENTOR(S) : Scott F. Rosebrough

It is certified that error appears in the above-indentified patent and that said Letters Patent is hereby corrected as shown below:

Column 18, line 34:

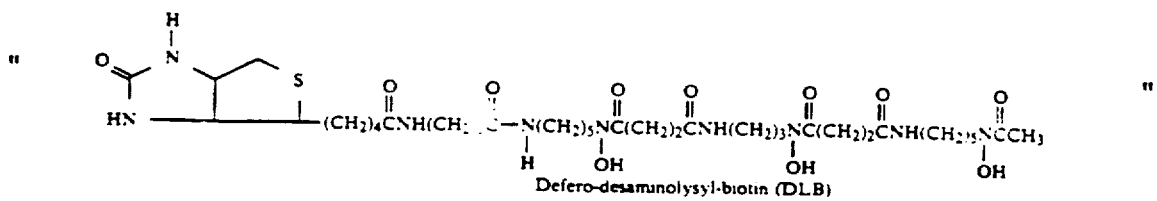

should read

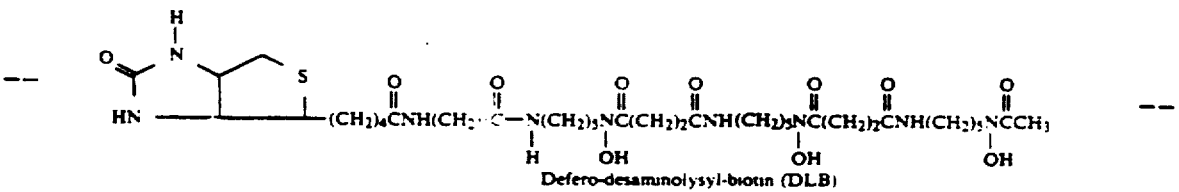

Signed and Sealed this

Thirtieth Day of April, 1996

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,326,778            Page 1 of 7
DATED : July 5, 1994
INVENTOR(S) : Scott F. Rosebrough It is certified that error appears in the above-indentified patent and that said Letters Patent is hereby corrected as shown below:

Column 5, lines 50-63:

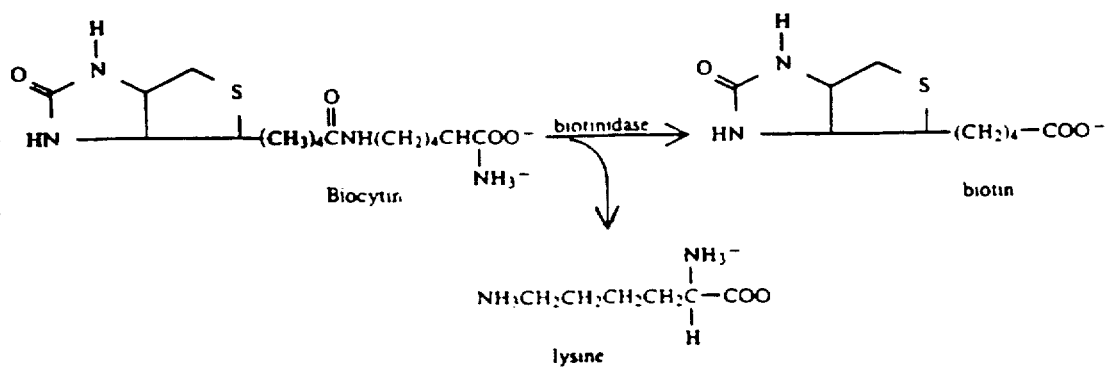

UNITED STATES PATENT AND TRADEMARK OFFICE
CERTIFICATE OF CORRECTION

PATENT NO.  : 5,326,778
DATED       : July 5, 1994
INVENTOR(S) : Scott F. Rosebrough It is certified that error appears in the above-indentified patent and that said Letters Patent is hereby corrected as shown below:

should read

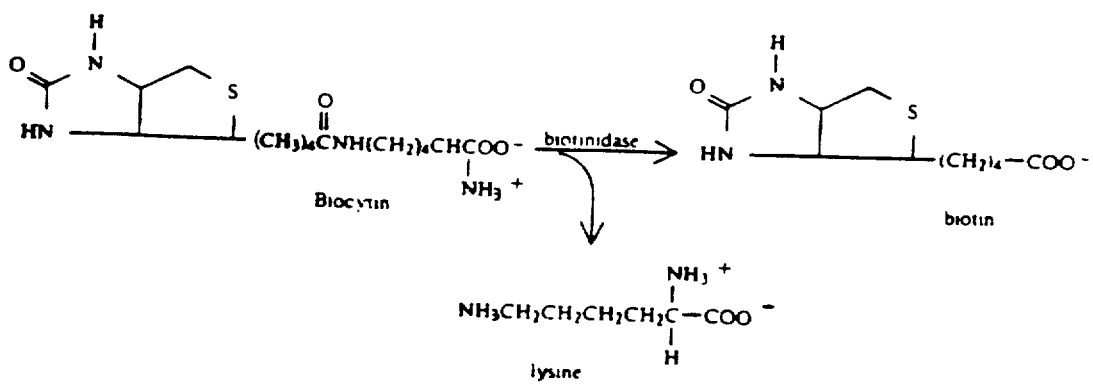

UNITED STATES PATENT AND TRADEMARK OFFICE
CERTIFICATE OF CORRECTION

PATENT NO. : 5,326,778   Page 3 of 7
DATED : July 5, 1994
INVENTOR(S) : Scott F. Rosebrough It is certified that error appears in the above-indentified patent and that said Letters Patent is hereby corrected as shown below:

Column 10, lines 13-23:

Scheme II

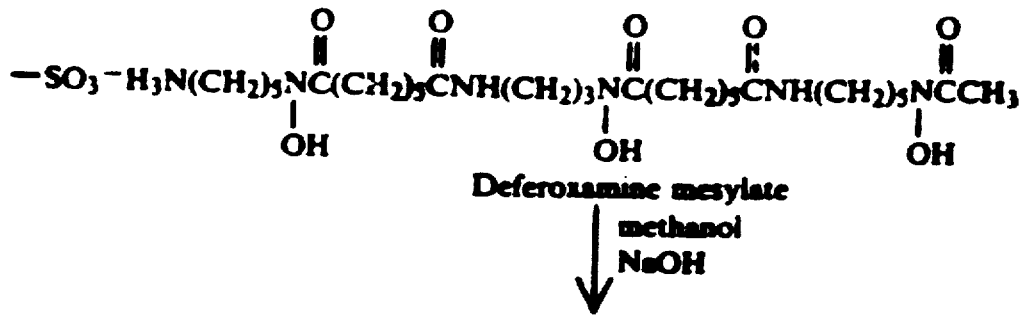

should read

Scheme II

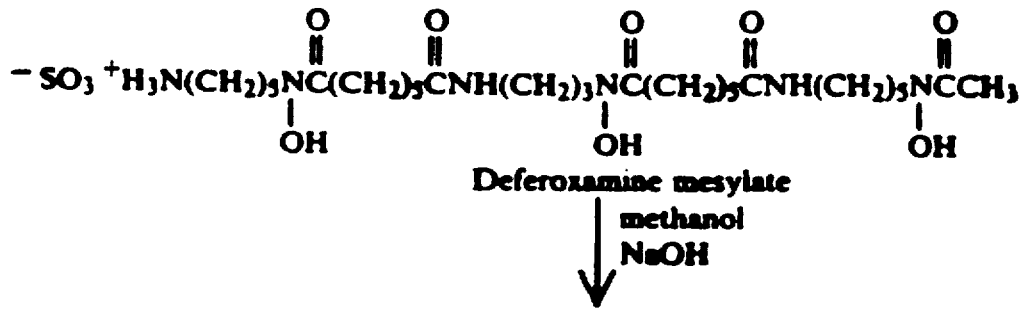

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

Column 12, lines 34-68:

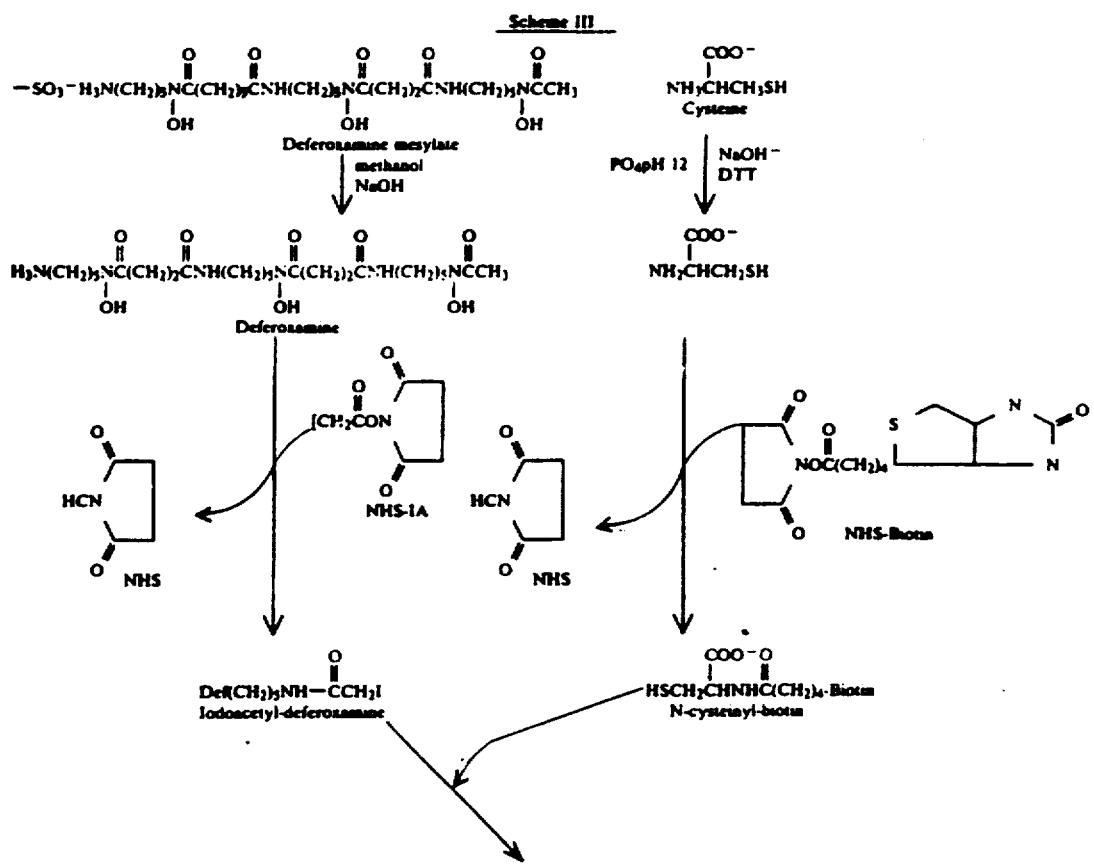

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

should read

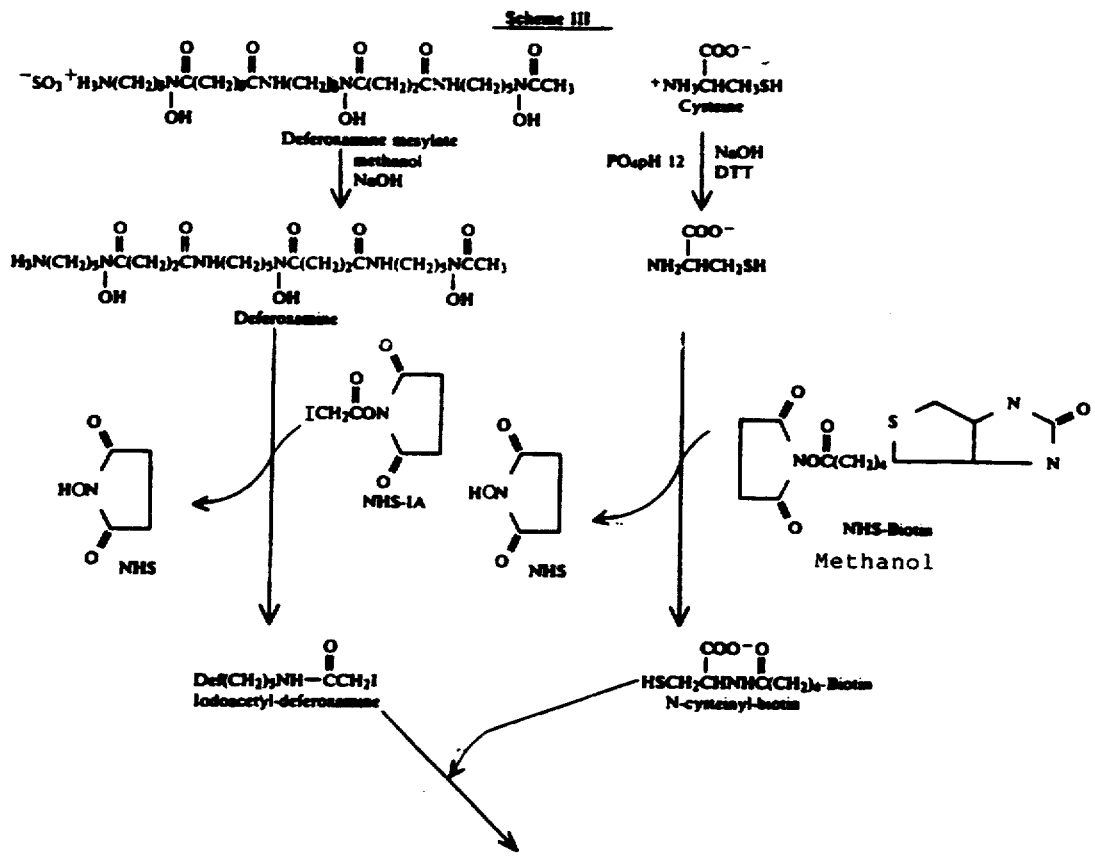

UNITED STATES PATENT AND TRADEMARK OFFICE
CERTIFICATE OF CORRECTION

PATENT NO. : 5,326,778

DATED : July 5, 1994

INVENTOR(S) : Scott F. Rosebrough

It is certified that error appears in the above-indentified patent and that said Letters Patent is hereby corrected as shown below:

Column 18, lines 3-13:

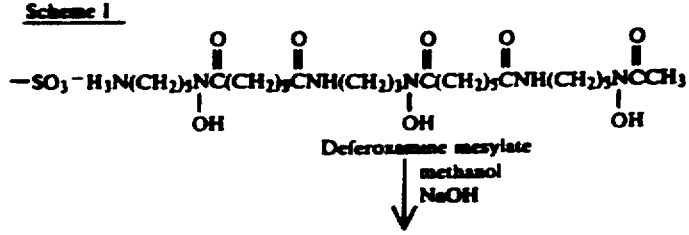

should read

UNITED STATES PATENT AND TRADEMARK OFFICE
CERTIFICATE OF CORRECTION

PATENT NO. : 5,326,778
DATED : July 5, 1994
INVENTOR(S) : Scott F. Rosebrough

It is certified that error appears in the above-indentified patent and that said Letters Patent is hereby corrected as shown below:

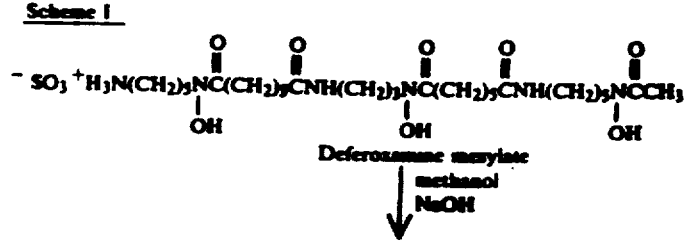

Signed and Sealed this

Sixth Day of August, 1996

*Attest:*

BRUCE LEHMAN

*Attesting Officer*     Commissioner of Patents and Trademarks